United States Patent [19]
Kanda et al.

[11] Patent Number: 5,348,013
[45] Date of Patent: Sep. 20, 1994

[54] ULTRASONIC DIAGNOSTIC APPARATUS CAPABLE OF ACQUIRING HIGH QUALITY IMAGE BY CORRECTING PHASE DISTORTION CONTAINED IN ULTRASONIC PULSES

[75] Inventors: Ryoichi Kanda, Ootawara; Yoichi Sumino, Nishinasuno, both of Japan

[73] Assignee: Kabushiki Kaisha Toshiba, Kanagawa, Japan

[21] Appl. No.: 750,599

[22] Filed: Aug. 28, 1991

[30] Foreign Application Priority Data

| Aug. 29, 1990 | [JP] | Japan | 2-225227 |
| Aug. 30, 1990 | [JP] | Japan | 2-228843 |
| Sep. 10, 1990 | [JP] | Japan | 2-237131 |
| Nov. 9, 1990 | [JP] | Japan | 2-305633 |
| Aug. 12, 1991 | [JP] | Japan | 3-201010 |
| Aug. 14, 1991 | [JP] | Japan | 3-204284 |

[51] Int. Cl.$^5$ .................................. A61B 8/00
[52] U.S. Cl. .................................. 128/660.07
[58] Field of Search ............. 128/660.01, 660.06, 128/660.07, 661.03; 73/625–628

[56] References Cited

U.S. PATENT DOCUMENTS

| 4,817,619 | 4/1989 | Sugiyama et al. | 128/661.09 |
| 4,989,143 | 1/1991 | O'Donnell et al. | 128/661.01 X |
| 5,184,623 | 2/1993 | Mallart | 128/661.01 |

FOREIGN PATENT DOCUMENTS

| 0139242A2 | 5/1985 | European Pat. Off. |
| 0256481A1 | 2/1988 | European Pat. Off. |
| 3742724A1 | 7/1988 | Fed. Rep. of Germany |
| 63-51846 | 3/0488 | Japan |

OTHER PUBLICATIONS

English language summary of Japanese Patent No. 63-51846.

*Primary Examiner*—Francis Jaworski
*Attorney, Agent, or Firm*—Finnegan, Henderson Farabow, Garrett & Dunner

[57] ABSTRACT

In an ultrasonic diagnostic apparatus, ultrasonic propagation time differences contained in echo signals reflected from a biological body under medical examination are corrected by comprising: a quadrature phase detecting unit for quadrature-phase-detecting the echo signals derived from an ultrasonic transducer probe to obtain as phase data a quadrature signal component and an in-phase signal component; a delay-time correcting value calculating unit for calculating at least one of delay-time correcting values used for the energizing signals and the echo signals based upon both of the quadrature signal component and in-phase signal component; and, a delay controlling unit for controlling at least one of delay time data previously given to the energizing signals anti echo signals based upon one of calculated delay-time correcting values.

22 Claims, 33 Drawing Sheets

FIG. 8

| | | | | | | | |
|---|---|---|---|---|---|---|---|
| IMAGE CONSTRUCTIVE UNIT | | 1 | 2 | 3 | 4 | 5 | |
| PHASE DETCTION | | | 1 | 2 | 3 | 4 | 5 |
| CONVERSION | | | | 1 | 2 | 3 | 4 |
| INTERPOLATION | | | | | 1 | 2 | 3 |
| RAM 22a | W-1-A | R/W-1-B | R-1-C | W-4-A | W-4-B | | |
| RAM 22b | | W-2-A | R/W-2-B | R-2-C | W-5-A | | |
| RAM 22c | | | W-3-A | R/W-3-B | R-3-C | | |

PHASE DISTORTION PATTERN

FUNCTION: $H_1(i)$

FUNCTION: $H_2(j)$

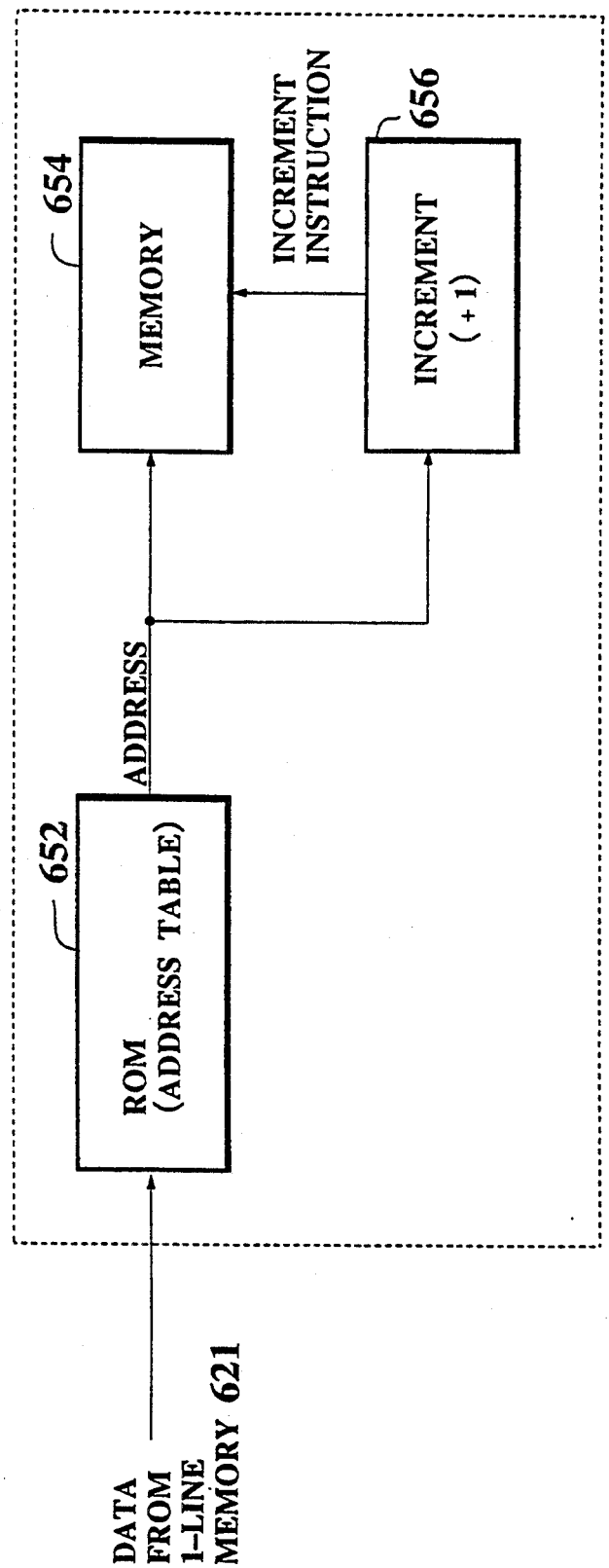
FIG.37 HISTOGRAM FORMING CIRCUIT 650

CHOLECYSTICS 606
700
BLOOD VESSEL 605
LINE "B"   LINE "A"

$S_A$
$S_B$

GOOD | NO GOOD | GOOD | NO GOOD | GOOD

JUDGMENT RESULTS

AVERAGE OF ENVELOPE SB

THRESHOLD LEVEL "$V_T$"

ULTRASONIC DIAGNOSTIC APPARATUS CAPABLE OF ACQUIRING HIGH QUALITY IMAGE BY CORRECTING PHASE DISTORTION CONTAINED IN ULTRASONIC PULSES

BACKGROUND OF THE INVENTION

1. Field of the Invention

The present invention generally relates to an ultrasonic diagnostic apparatus for acquiring ultrasonic images of a biological body by applying delay times to energizing signals for a plurality of transducer elements arranged in an array form, and also to echo signals reflected from interiors of the biological body. More specifically, the present Invention is directed to an ultrasonic diagnostic apparatus capable of improving image qualities of the acquired ultrasonic images with respect to unequal portions within the biological body based upon fluctuations in arrival times of the echo signals.

2. Description of the Prior Art

In a typical ultrasonic diagnostic apparatus, a plurality of transducer elements are arranged in an array form. Data on delay times which are determined based on geometrical positional information with respect to the respective transducer elements, are electrically given to both the energizing signals and echo signals reflected from interiors of a biological body. The energizing signals are used to transmit ultrasonic pulses from the transducer elements toward the biological body. Based upon the delay time data, a focal point of the, echo signals is defined by the known in-phase additional process so as to obtain a desirable ultrasonic image of the biological body. The focal point is scanned under electronic scanning control, for instance, In a plane form. More specifically, while several tens to several hundreds of rasters are transmitted/receiver, a "B-mode" ultrasonic image is obtained in an image constructive unit.

The above-described known ultrasonic imaging technique will now be described more in detail with reference to FIGS. 1 to 3.

As shown in FIG. 1, under such conditions that the velocity of sound which passes through a propagation medium $I_o$ from a transducer element "V" to a focal point is uniform, and this sound velocity is known, when the respective transducer elements are energized by receiving data on delay times "$d_1$" to "$d_n$" ("n" being an integer greater than 2) which has been defined based on the focal point "C" and the geometric positional data, a focal point "C" at which ultrasonic pulses are fully focused can be formed without serious phase shifts.

However, in case that organs within a biological body "P" are to be ultrasonic-imaged, as represented in FIG. 2, the ultrasonic pulses transmitted from the transducer elements "V" are propagated through a surface layer "$P_f$" biological body "P", which is constructed of fat and muscle made of unequal propagation mediums I and II. If the delay times "$d_1$" to "$d_n$" are given to process the energizing signals for the transducer elements "V" is a similar method as in FIG. 1, there are phase shifts in the ultrasonic pulses near another focal point C'. As a result, this focal point C' is widened, as compared with the first-mentioned focal point C, and also both special resolution and contrast resolution of the resultant ultrasonic image are lowered.

Also to form such a sufficiently focused point "C", even when the organs having the unequal propagation mediums I and II are ultrasonic-imaged without any phase shift, it has been proposed that the delay correction values which have been obtained by way of the conventional correlation method, are added to the delay times determined by the geometric positional information on the respective transducer elements and this focal point C. Thus, the image characteristics of the ultrasonic images are improved. This conventional correlation method is described in, for example, Japanese Patent Disclosure 53-51846 (1988).

In accordance with one of the conventional correlation, as illustrated in FIG. 3, after the correlation function "F" has been calculated with respect to one pair of echo signals received by two certain transducer elements (see FIG. 2), time "$t_p$" indicative peak value "$F_p$" in this correlation function "F" is found out; a time difference "$\Delta t$" between this time "$t_p$" and a predetermined reference time "$t_o$" is calculated; and then the delay times produced in the echo signals received by two certain transducer elements are corrected based on this time difference information "$\Delta t$".

However, since the above-described conventional correlation method requires an extremely large computation scale, there are first problems that this correlation method is not suitable for improving the realtime image processing and impedes a compactness of the ultrasonic diagnostic apparatus.

On the other hand, it is impossible to consider another delay correction method with respect to plural focal points.

As shown in FIG. 4, when ultrasonic pulse beams are focused onto two focal points "0" and "Q" of the biological body "P" which are positioned along a depth direction of this body by employing an ultrasonic probe "$P_b$" having "M" pieces of transducer elements, tile propagation paths these ultrasonic pulse beams are different from each other. In such a case, delay correction values different from each other are required with respect to two focal points "0" and "Q" by measuring the phase differences (i.e., time difference in propagation) of the echo signals.

In actual, not only two focal points "0", "Q", but also many other focal points are present within the biological body "P". Assuming now that a total number of ultrasonic scanning beams is "i" and a total number of focal points along each of the ultrasonic scanning beams is "j", a total focal point of this biological body "P" to be imaged amounts to 1×J. Normally, "1"=100 to 300 and "j"=10 to 30. Accordingly, the entire focal points amount to 1000 to 9000.

There is a second problem that a large quantity delay correction values must be calculated based on the conventional correlation method, which is not practically possible.

Furthermore, there are non-reflection (non-echo) portions within a biological body such as cholecystics and blood vessels, from which ultrasonic beams are not reflected as the echo pulses. If a focal point to ultrasonic-imaged is selected at cholecystics, no reflection signal (echo signal) is obtained therefrom, that no delay correction value of this focused cholecystics portion is calculated. Accordingly, there is a third problem that reflection signals suitable for ultrasonic measurements are not always obtained.

SUMMARY OF THE INVENTION

As a consequence, an object of the present invention is to provide such an ultrasonic diagnostic apparatus capable of improving a deteriorated ultrasonic image quality in a real time.

Another object of the present invention is to provide an ultrasonic diagnostic apparatus capable of forming a focal point within a biological body without any phase shift.

A further object of the present Invention is to provide an ultrasonic diagnostic apparatus capable of correctly evaluating echo signals reflected from various biological conditions of a biological body.

Still, a further object of the present invention is to provide an ultrasonic diagnostic apparatus capable of precisely correct delay amounts of transmitting-/received signals, namely, fluctuation contained in signal propagation time.

To achieve the above-described objects and other features, an ultrasonic diagnostic apparatus (1000:2000:3000:4000), according to the present invention comprises:

ultrasonic diagnostic means (2) having a plurality of ultrasonic transducer elements (V:43) for transmitting ultrasonic pulses to an object under medical examination in response to energizing signals, and for receiving echoes therefrom to produce echo signals;

quadrature phase detecting means (30:130:25) for quadrature-phase-detecting the echo signals derived from the transducer means (2) to obtain as phase data a quadrature signal component and an in-phase signal component;

delay-time correcting value calculating means (23) for calculating at least one of delay-time correcting values used for the energizing signals and the echo signals based upon both of the quadrature signal component and in-phase signal component; and, delay controlling means (13) for controlling at least one of delay time data previously given to the energizing signals and echo signals based upon said one of calculated delay-time correcting values.

An ultrasonic diagnostic apparatus (5000), according to the present invention, comprises:

ultrasonic transducer means (20) having a plurality of transducer elements for transmitting ultrasonic pulses to a specific region within an object under medical examination in response to energizing signals, and for receiving echoes from the specific region to produce echo signals;

first delay-time correcting value calculating means (300) for calculating first delay-time correcting values with respect to first transmitting/receiving delay times for the respective transducer elements by calculating propagation time differences among the echo signals from focal points of the ultrasonic pulses within the specific region;

second delay-time correcting value calculating means (400) for calculating second delay-time correcting values with respect to second transmitting/receiving delay times for the transducer elements used to receive the echo signals from a region other than the specific region by interpolating the first delay-time correcting values; and, delay controlling means (53) for controlling predetermined transmitting/receiving delay times with respect to said specific region based on said first delay-time correcting values and also with respect to said region other than said specific region based on said second delay-time correcting values.

Furthermore, an ultrasonic diagnostic apparatus (6000:7000), according to the present invention, comprises:

ultrasonic transducer means (601) having a plurality of ultrasonic transducer elements (601a:601n), for transmitting ultrasonic pulses to an object under medical examination in response to energizing signals, and for receiving echoes therefrom to produce echo signals;

judging means (622:623) for judging whether or not the received echo signals are valid data used to correct delay times for the energizing signals and echo signals;

phase-distortion detecting means (614) for detecting phase distortion contained in the echo signals acquired when said judging means (622:650) judges that the received echo signals are valid data;

delay-time correcting value calculating means (616) for calculating at least one of transmission/reception delay-time correcting values based on a result of the phase-distortion detecting means (614); and, delay controlling means (610:613) for controlling at least one of transmission/reception delay time data previously given to the energizing signals and echo signals based on said one of calculated transmission/reception delay-time correcting values.

Also, an ultrasonic diagnostic apparatus (8000), according to the present invention, comprises:

ultrasonic transducer means (810) having a plurality of ultrasonic transducer elements (801), for transmitting ultrasonic pulses to an object under medical examination in response to energizing signals, and for receiving echoes therefrom to produce echo signals;

propagation-time-difference detecting means (814) for detecting propagation time differences among the echo signals derived from the transducer elements (801) as propagation time distribution data;

delay-time value calculating means (817) for calculating first delay-time correcting values with respect to previously set transmission/reception delay time data based on the detected propagation time difference data;

eliminating means (815) for eliminating an unwanted signal component representative of unwanted reflecting articles within the biological body from the propagation time difference data thereby to obtain second delay-time correcting values; and, delay controlling means (812:813) for controlling delay time data previously given to the energizing signals and echo signals by correcting said first delay-time correcting values based on said second delay-time correcting values.

Moreover, an ultrasonic diagnostic apparatus (9000, according to the present invention, comprises:

ultrasonic transducer means (601) having a plurality of ultrasonic transducer elements (601a:601n) for transmitting ultrasonic pulses to an object under medical examination in response to energizing signals, and for receiving echoes therefrom to produce echo signals;

propagation-time-difference detecting means (614) for detecting first propagation time differences among the echo signals derived via the transducer elements (601a:601n) from the biological body;

delay-time correcting value calculating means (930) for calculating transmission/reception delay-time correcting values based on the detected propagation-time differences;

calibraion value calculating means (930:940) for previously measuring second propagation time differences among the echo signals derived via the transducer elements from a phamton (900) having characteristics substantially equivalent to ultrasonic attenuation characteristics of said biological body and for storing said second propagation time differences as delay-time calibration values; and, delay controlling means (980) for controlling delay-time data previously given to the energizing signals and echo signals based upon said transmission/reception delay-time correcting values and said delay-time calibration values.

BRIEF DESCRIPTION OF THE DRAWINGS

For a better understanding of these and other objects of the present invention, reference is made of the following detailed description of the invention to be read in conjunction with the following drawings, in which:

FIGS. 6 to 8 illustrate operations of the first ultrasonic diagnostic apparatus 1000;

FIGS. 36A to 37 represent operations of the sixth ultrasonic diagnostic apparatus 6000;

DETAILED DESCRIPTION OF THE PREFERRED EMBODIMENTS

FIRST BASIC IDEA

Before describing various types of preferred embodiments, a first basic idea of an ultrasonic diagnostic apparatus according to the present invention will now be summarized.

When a phase detecting means processes reception signals (i.e., echo signals) received by a plurality of transducer elements so as to detect phases of the respective echo signals, a converting means will convert these phase data into corresponding delay time data. Then, a correcting means corrects a predetermined delay time based on the converted delay time data, whereby since the corrected delay times corresponding to propagation mediums of a biological body under medical examination are electronically applied to both the energizing signals and echo (reflection) signals for the plural transducer elements, a focal point can be formed with a slight phase shift.

In case that the phase data outputted from the phase detecting means contains discontinuities along the array direction of the transducer elements, a phase correcting means corrects these phase discontinuities to obtain phase continuities. As a result, the correct phase data having no error caused by these discontinuities may be inputted into the converting means.

Furthermore, a control means controls data write-/read-operations to a plurality of memories, and also controls such that the delay time data obtained by way of the predetermined calculating process are applied to both the energizing signals and echo signals so as to newly acquire ultrasonic images of the biological body, whereby a focal point with a less phase shift can be formed in a real time.

ARRANGEMENT OF FIRST ULTRASONIC DIAGNOSTIC APPARATUS

I. OVERALL ARRANGEMENT

Figure 5:
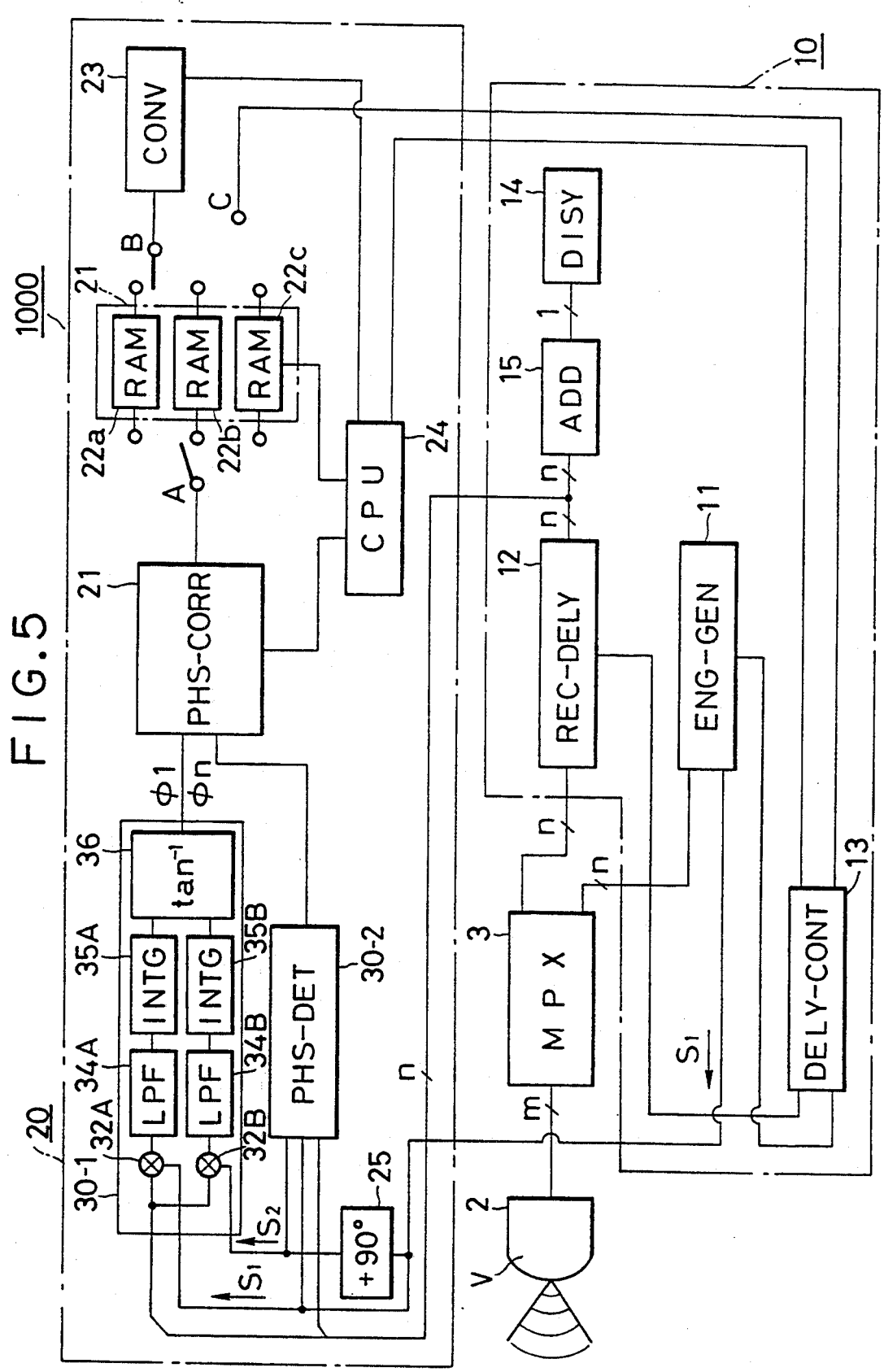
FIG. 5 is a schematic block diagram for showing an arrangement of an ultrasonic diagnostic apparatus 1000 according to a first preferred embodiment of the present invention.

In FIG. 5, there is shown an ultrasonic diagnostic apparatus 1000 according to a first preferred embodiment of the present invention, that is realized by utilizing the above-described first basic idea of the present invention.

Figure 1:
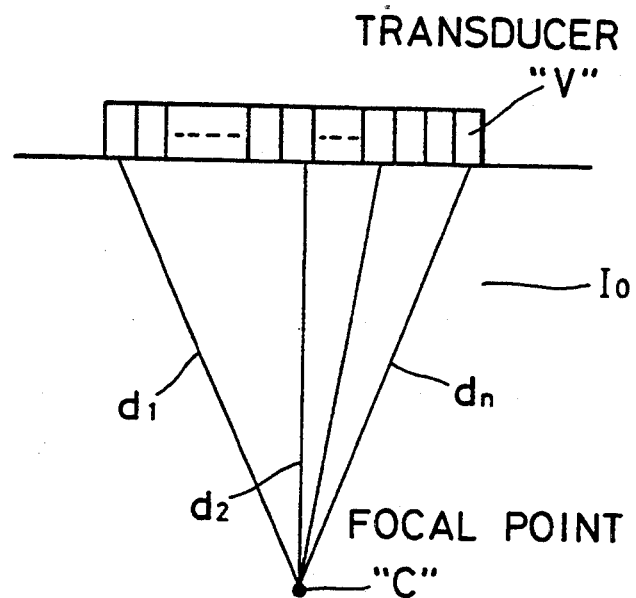
FIGS. 1 to 4 are illustrations for explaining widened focal points of the conventional ultrasonic diagnostic apparatus.
Figure 2:
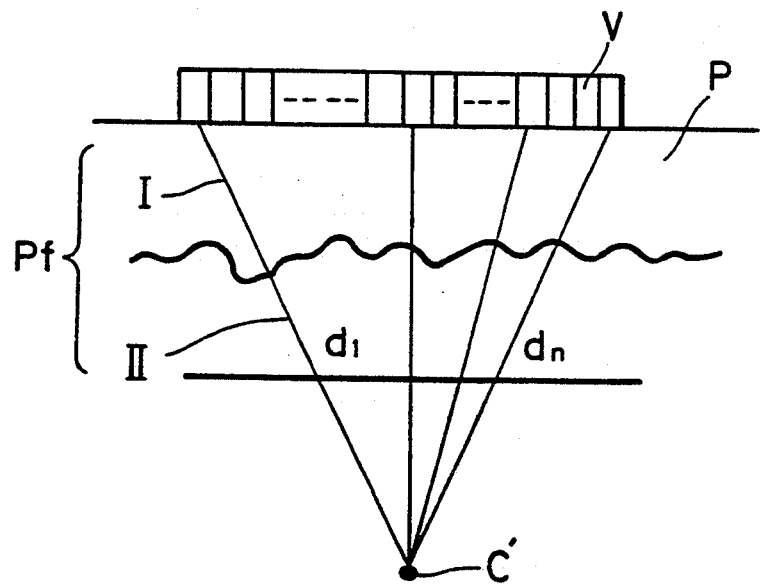
Figure 3:
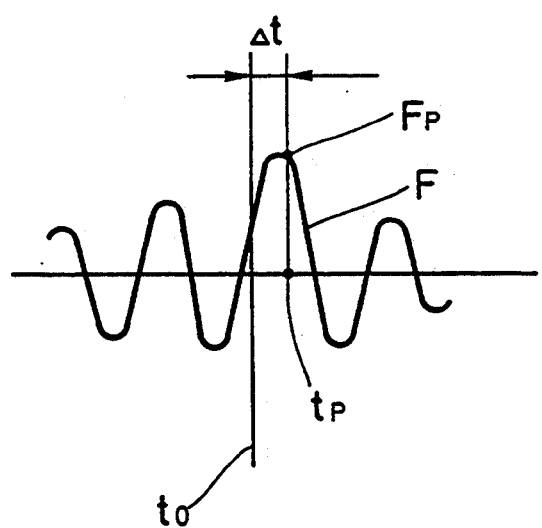
Figure 4:
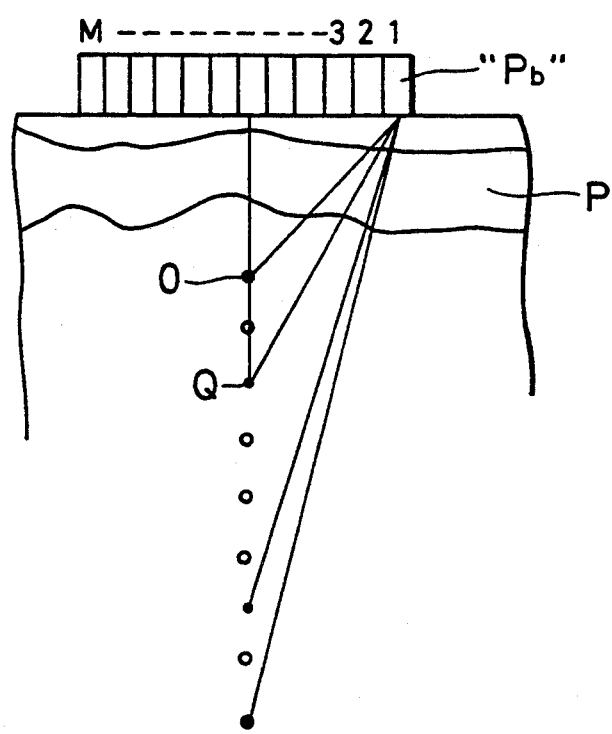

The first ultrasonic diagnostic apparatus 1000 mainly comprises an ultrasonic probe 2 having a plurality of transducer elements V arranged-in an array form (as shown in FIG. 1); a multiplexer 3 for sequentially energizing the plural transducer elements V; a display system 10 for displaying an ultrasonic image of a biological body under medical examination (not shown in detail) in response to echo signals derived from the transducer elements V; and a signal correction system 20 for correcting delay times of energizing signals and echo (reception) signals of the transducer elements.

More specifically, the display unit 10 includes an energizing signal generating section 11 for producing the energizing signals having a predetermined central frequency, e.g., 3 MHz with a narrow bandwidth, an also a reference signal "$S_1$" to be supplied to the signal correction system 10; a reception delay circuit 12 for applying a predetermined delay time to the echo signals; an adder 15 for performing an addition process with respect to these signals; and a delay control section 13 having a delay time memory (not shown in detail), for applying delay times to the above-described energizing signal generating circuit 11 and reception delay circuit 12; and furthermore a display section 14 equipped with a television monitor (not shown in detail) for displaying ultrasonic images of the biological body thereon. Into the delay time memory employed in this delay control section 13, predetermined delay time data produced based on geometric positional information about the transducer elements V are stored, which are supplied to the signal correction system 20 in order that the corrected delay times are produced and used in the energizing-signal generating section 11 and reception delay circuit 12.

It should be noted that a total number of these transducer elements V is selected to be "m" ("m" being an integer greater than 2) in this preferred embodiment, and therefore "m" pieces of echo signals are received by the transducer elements V.

The signal correction system 20 includes a phase detecting section 30 for detecting phases of the received echo signals by processing the echo signals received from the probe 2 via the multiplexer 3; a phase correcting section 21 for correcting discontinuities contained in the phase data detected by the phase detecting unit 30; a storage unit 22 for storing therein continuous phase data which are obtained from the phase correcting unit 21; and a converting section 23 for performing one process to convert the data and the other process to interpolate the data. The signal correction system 20 further includes a central processing unit 24 which may function as a correction means for correcting the delay time data stored in the delay time memory of the delay control section 13 based on the delay time data converted by the converting section 23; and a 90°-phase shifter 25.

The phase detecting sections 30-1 and 30-2 are employed so as to detect phase information as ultrasonic Doppler information, which is well known in the art. One phase detecting section 30-1 is constructed of a first mixer 32A, a second mixer 32B, a first low-pass filter 34A, a second low-pass filter 34B, a first integrator 35A, a second integrator 35B, and an arc tangent ($\tan^{-1}$) circuit 36. The first mixer 32A mixes a signal "S" derived from the reception delay circuit 12 with a reference signal "(cos $\omega t$) $S_1$" that is synchronized with the energizing signal outputted from the energizing signal generating section 11. The second mixer 32A mixes the above-described signal "S" derived from the reception delay circuit 12 with a signal (sin $\omega t$) $S_2$ which is produced by phase-shifting the reference signal $S_1$ from the energizing signal generating section 11 in the 90°-phase shifter 25 by 90°. These signal phase correcting sections 30-1 and 30-2 perform the above-described signal process by inputting therein the reception signals "S" with respect to all rasters or every several rasters.

It should be noted that the angular frequency "$\omega$" of two reference signals (cos $\omega t$) $S_1$ and (sin $\omega t$) $S_2$ supplied from the energizing signal generating section 11 to the first and second mixers 32A and 32B, are selected to be one of frequencies of the reception (echo) signal "S". The function of the first and second integrators 35A and 35B is to integrate the echo signals, thereby obtaining an averaged phase within a certain range of the reception signals.

II. SIGNAL CORRECTING SYSTEM

With respect to the respective arrangements in the signal correcting system 20, the following description will be made of such an example where a reception (echo) signal "$S_k(t)$" is received by a k-th transducer element of the probe 2 ("k" being an integer smaller than "m").

Assuming now that an amplitude of this echo signal $S_k(t)$ is $A_k(t)$ and a phase thereof is $\phi_k$, the reception signal $S_k(t)$ received by the k-th transducer element (not shown in detail) is expressed by:

$$S_k(t) = A_k(t)\cos(\omega t + \phi_k) \tag{1}$$

This echo signal $S_k(t)$ is mixed with the above-described reference signals $S_1$ and $S_2$ in the first and second mixers 32A and 32B, respectively. When the mixed signal is expressed as a complex signal $Z_k(t)$, it is given:

$$Z_k(t) = A_k(t) \cdot [\cos(2\omega t + \phi_k) + \cos(\phi_k)] + j\{A_k(t) \cdot [\sin(\phi_k) - \sin(2\omega t + \phi_k)]\} \tag{2}$$

Furthermore, when this complex signal $Z_k(t)$ is filtered in the respective low pass filters 34A and 34B in order to remove a high frequency signal component of "$2\omega$" by the first or second low pass filters 34A or 34B, another complex signal $Z_k(t)$ is outputted from the relevant low-pass filter 34A, 34B, which is expressed by the following equation (3):

$$Z_k(t) = A_k(t)\cos(\phi_k) + j\{A_k(t)\sin(\phi_k)\} \tag{3}$$

Thereafter, this complex signal $Z_k(t)$ outputted from the low-pass filter 34A or 34B is calculated in the arc tangent circuit 36 in accordance with the following equation (4), whereby phase data "$\phi_k$" is obtained therefrom and is supplied to the phase correcting section 21:

$$\begin{aligned}\phi_k &= \tan^{-}\{[A_k(t)\sin(\phi_k)]/[A_k(t)\cos(\phi_k)]\} \\ &= \tan^{-}\{[\sin(\phi_k)/\cos(\phi_k)\} \\ &= \tan^{-}\{[\tan(\phi_k)\}\end{aligned}$$

Figure 6:
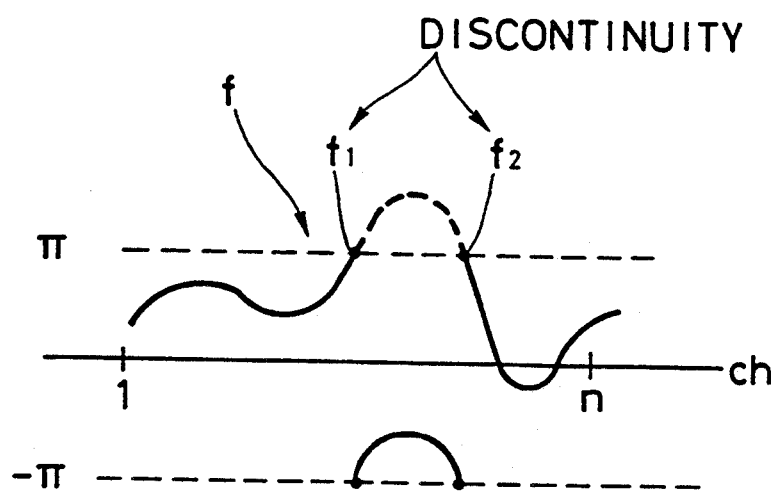
Figure 7:
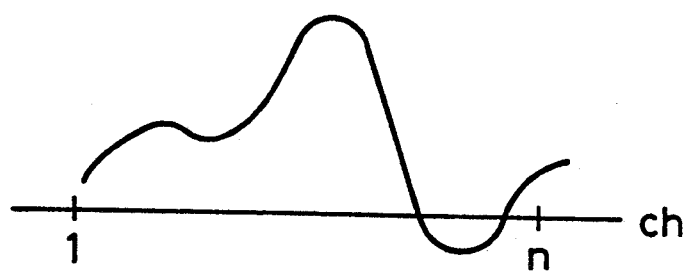

As previously explained, "n" pieces of phase data ($\phi_1$ to $\phi_n$) are inputted into the phase correcting section 21 within a phase range from "$-\pi$" to "$+\pi$", as shown in FIG. 6. The function of this phase correcting section 21 is to couple discontinuities f ($f_1$, $f_2$) with each other contained in the phase distribution data under control of CPU 24. As shown in FIG. 6, these discontinuities f ($f_1$, $f_2$) are coupled with each other and then are obtained as the continuous phase distribution data as shown in FIG. 7. The continuous phase distribution data are supplied to the respective storage sections 22 (22a to 22c) every image constructive unit.

III. STORAGE & CONVERTING SECTIONS

As represented in FIG. 5, the storage section 22 employs three RAMs 22a to 22c. Under control of CPU 24, changing switches "A", "B" and "C" are operated every one image constructive unit in order that both the phase data from the phase correcting section 21, and the delay time data which has been converted and interpolated by the converting section 23 are sequentially written into these RAMs 22a to 22c. The function of the converting unit 23 is to convert the phase data obtained by all rasters, or several rasters into delay time data, and also to interpolate the delay time data with respect to the skipped (or not processed) several rasters while acquiring the phase data every several rasters. Under control of CPU 24, the predetermined delay time data stored in the delay time memory of the delay time control unit 13, is corrected every one image constructive unit based on the converted/interpolated delay time data.

OVERALL OPERATION OF FIRST ULTRASONIC DIAGNOSTIC APPARATUS

An overall operation of the first ultrasonic diagnostic apparatus 1000 will now be described with reference to the above-described FIGS. 5 to 7 together with FIG. 8 showing contents of the data process and memories.

Upon commencement of ultrasonic imaging operation by attaching the ultrasonic probe 2 to a surface of the biological body, an ultrasonic image of the biological body is acquired by the first ultrasonic diagnostic apparatus 1000, for instance, in a B-mode under control of CPU 24. The delay control section 13 delay-controls the energizing signal generating section 11 and adder 15 based on the predetermined delay time data stored in the delay time memory employed therein. The probe 2 performs B-mode scanning operation with respect to first image constructive unit under control of CPU 24. Accordingly, a B-mode ultrasonic image of the first image constructive unit is displayed on the TV monitor of the display section 14 employed in the display system 10. It should be noted that at this stage, since the predetermined delay time data have not yet been corrected in accordance with the propagation mediums within the biological body, the sufficiently focused focal point is formed, resulting in lowered space resolution.

Subsequently, B-mode images are successively displayed on the TV monitor of the display section 14 after second and subsequent image constructive units. According to the feature of this first ultrasonic diagnostic apparatus 1000, when the B-mode image data on the first image constructive unit is acquired, the signal correction system 20 calculates delay times for correction purposes in response to the reception signal "S" from the multiplexer 3 and therefore corrects the predetermined delay time data which have been stored in the delay time memory of the delay control section 13 based on the calculated correcting delay times, thereby to obtain desirable delay times corrected by taking account of the propagation mediums constructing the biological body.

SIGNAL CORRECTION

The process of the signal correcting system 20 will now be described more in detail.

FIG. 8 represents contents of the signal process operations and of the memory RAMs 22a to 22c with respect to the image constructive unit. In FIG. 8, symbol "W" indicates write operation of data into RAMs 22a to 22c; symbol "R" denotes read operation of data from RAMs 22a to 22c; reference numerals written with these symbols "W" and "R" indicate numbers of the image constructive unit; and symbols "A", "B", "C" represent switching operations of the switches A to C (see FIG. 5).

During the B-mode scanning operation for the first image constructive unit, the received (echo) signals are phase-detected by the phase detective section 30 and then the discontinuities ($f_1$, $f_2$) contained in the phase-detected echo signals are corrected by the phase correcting section 21 based upon the phase detected information, and the resultant image data are represented as "W-1-A". The image data "W-1-A" are written into RAM 22a while the switch "A" is actuated.

Next, while the B-mode scanning operation is performed for the second image constructive unit by energizing the probe 2, the converting section 23 receives the phase-corrected data "R/W-1-B" which have been previously written into the RAM 22a and acquired based on the phase-corrected data on the first image constructive unit. Then, the phase-detected data "R/W-1-B" are converted into the desirable delay time data by this converting section 23, which are written into the RAM 22a. On the other hand, the phase-corrected data on the second image constructive unit are represented as "W-2-A", which are derived from the phase correcting section 21, and written into RAM 22b by operating the switch "B".

Subsequently, while the B-mode scanning operation for the third image constructive unit is carried out by energizing the probe 2, the delay control section 13 reads out the delay time data on the first image constructive unit stored in RAM 22a, as indicated by "R-1-C", and performs the correction when the transmission/reception delay operations are actually performed. Thereafter, the phase-corrected data on the second image constructive unit stored into RAM 22b, as indicated as "R/W-2-B", are acquired and converted into the corresponding delay time data in the converting section 23. Also, these phase-corrected data are written into RAM 22b, and the phase-corrected data denoted by "W-3-A" are written from the phase correcting section 21 into RAM 22c by operating the switch "C".

Then, the desirable focal point with the less phase shift can be formed based upon this B-mode image scanning operation and therefore the B-mode images can be formed with the improved spatial resolution and contrast resolution on the display section 14. Subsequently, the image data on the third and subsequent image constructive units are similarly processed and the resultant processed image data are written/read from RAM 22a to 22c.

In accordance with the first ultrasonic diagnostic apparatus 1000, after the third image constructive unit, since the delay time data acquired under real time characteristics delayed for three image constructive units and corrected by taking account of the propagation medium of the biological body are electronically applied to both the energizing signals and echo signals of the transducer elements, the focal point with the small phase shift can be formed and the ultrasonic images with the better image quality can be obtained.

OVERALL ARRANGEMENT OF SECOND ULTRASONIC DIAGNOSTIC APPARATUS

Figure 9:
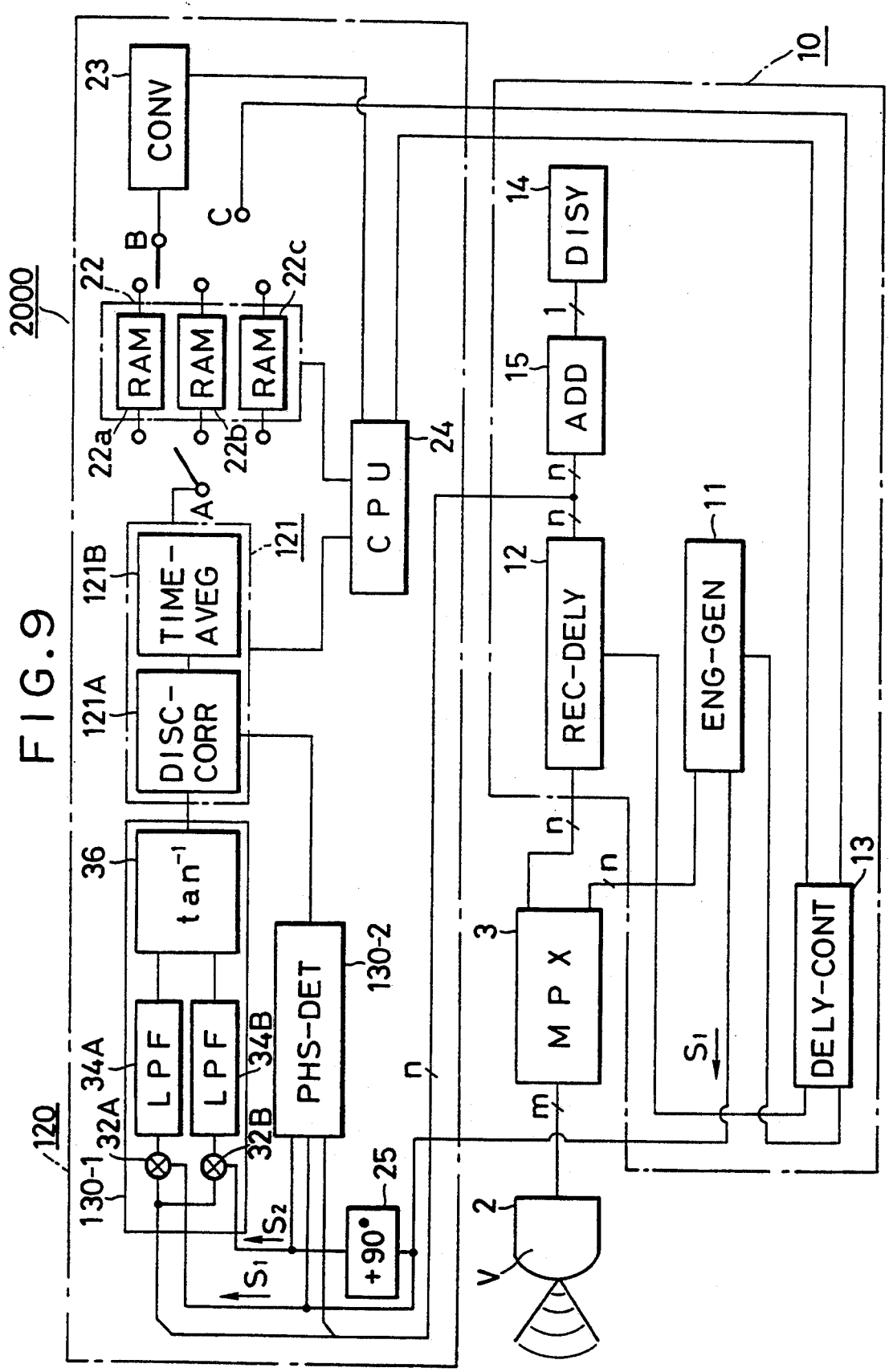
FIG. 9 is a schematic block diagram for showing an arrangement of an ultrasonic diagnostic apparatus 2000 according to a second preferred embodiment of the present invention.

FIG. 9 is a schematic block diagram of an ultrasonic diagnostic apparatus 2000 according to a second preferred embodiment of the present Invention. It should be noted that the same reference numerals shown in FIG. 5 will be employed as those for denoting the same circuit elements shown in the following figures. Also, this second ultrasonic diagnostic apparatus 2000 is realized based on the first basic idea of the present invention.

As apparent from FIG. 9, a major different construction of the second ultrasonic diagnostic apparatus 2000 from the first ultrasonic diagnostic apparatus 1000 is to newly employ a phase detecting section 130 and a phase correcting section 121 of a signal correcting system 120.

Figure 10:
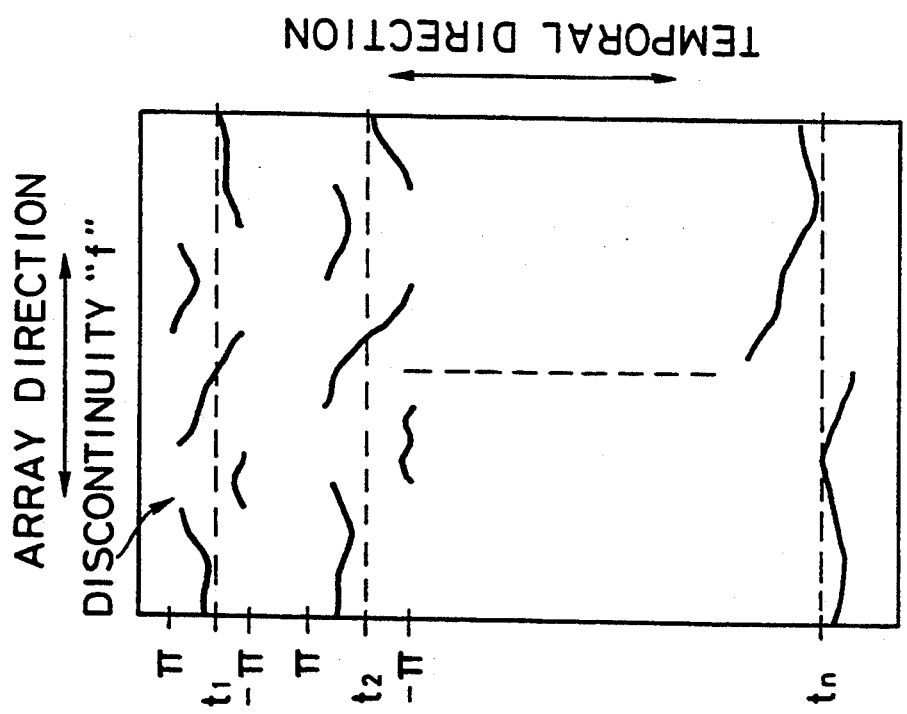

The phase detecting section 130 corresponds to the phase detecting section 30 of the first ultrasonic diagnostic apparatus 1000 from which the first and second integrators 35A and 35B are omitted. Since the integrators 35A and 35B are omitted from this phase detecting section 130, the function of this phase detecting section 130 is to obtain instantaneous phase data at time instants "$t_1$" to "$t_n$" as shown in FIG. 10. This drawing indicates a discontinuity "f" occurring at the respective time instants "$t_1$" to "$T_n$" along the array direction of the transducer elements V.

Figure 11:
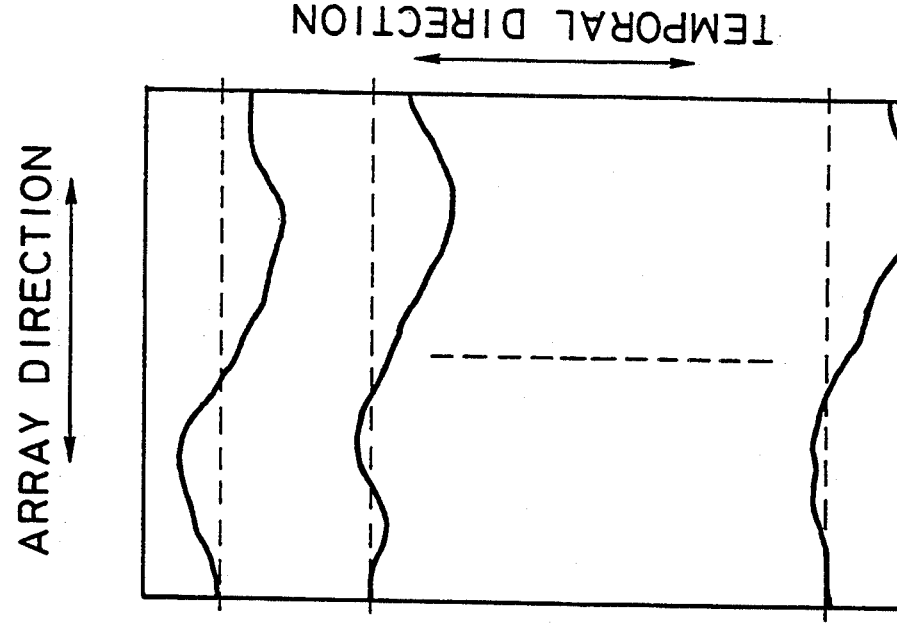
FIGS. 10 to 15 Illustrate operations of the second ultrasonic diagnostic apparatus 2000.
Figure 12:
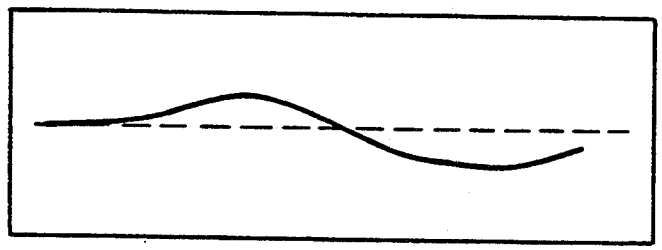

The above-described phase correcting section 121 is arranged by a discontinuity correction section 121A and a temporal direction averaging section 121B. The discontinuity correction section 121A corrects the discontinuities of the phase data (see FIG. 11) every time instants "$t_1$" to "$t_n$". The temporal direction averaging section 121B averages the phase data at the respective time instants "$t_1$" to "$t_n$" the discontinuities of which have been corrected, and obtains such a phase distortion pattern as shown in FIG. 12.

DISCONTINUITY CORRECTING OPERATION

The above-described discontinuity operation by the discontinuity correcting section 121A will now be described more in detail with reference to FIGS. 13 to 16. The major operation of this discontinuity correcting section 121A is such that after the discontinuity point "f" has been searched, a bias value is applied to the phase data at this discontinuity point "f" so as to obtain continuous phase data without any discontinuities.

Figure 13:
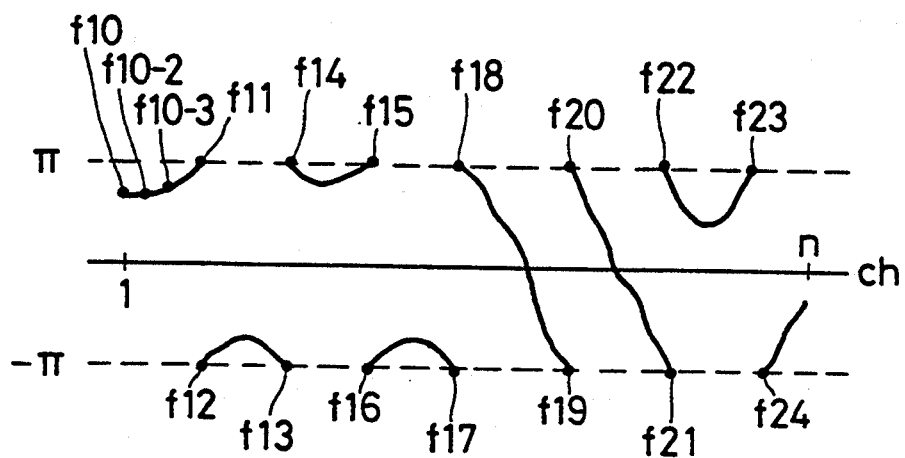

In a concrete example, first, a starting point "$f_{10}$" of the calculating process for the equation (5) is selected. It should be understood that although an end point at the left side of FIG. 13 is selected to be "$f_{10}$", any other points may be selected to be this end point. Also, it should be noted that a bias value at this starting point "$f_{10}$" is selected to be "0". The phase difference calculation is carried out is such a manner that a phase difference "$\Delta\phi$" is first calculated between the starting point "$f_{10}$" and the adjacent point "$f_{10-2}$", and subsequently, another phase difference $\Delta\phi$ is calculated between this point "$f_{10-2}$" and the adjacent point "$f_{10-3}$".

Figure 14:
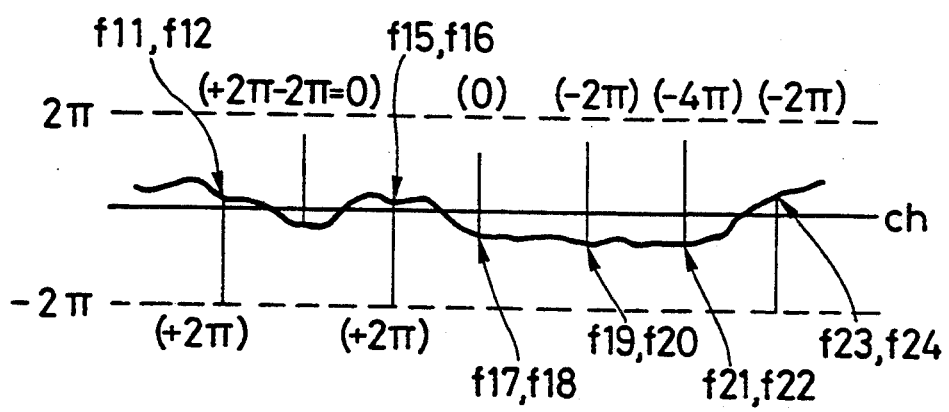

The calculation results are represented in FIG. 14. As apparent from FIG. 14, for Instance, at the discontinuity points $f_{11}$ and $f_{12}$, the following calculation result (6) is given:

$$\phi_3 - \phi_2 \approx -\pi - (+\pi) \approx -2\pi \quad (6)$$

Thus, as to the discontinuity points $f_{11}$ and $f_{12}$; $f_{15}$ and $f_{16}$; $f_{23}$ and $f_{24}$, which suddenly change from a positive to a negative, the calculation results become discontinuity points $f_{13}$ and $f_{14}$; $f_{17}$ and $f_{18}$; $f_{19}$ and $f_{20}$; $f_{21}$ and $f_{22}$, which suddenly change from a negative to a positive, the calculation results become $+2\pi$ approximately.

Figure 15:
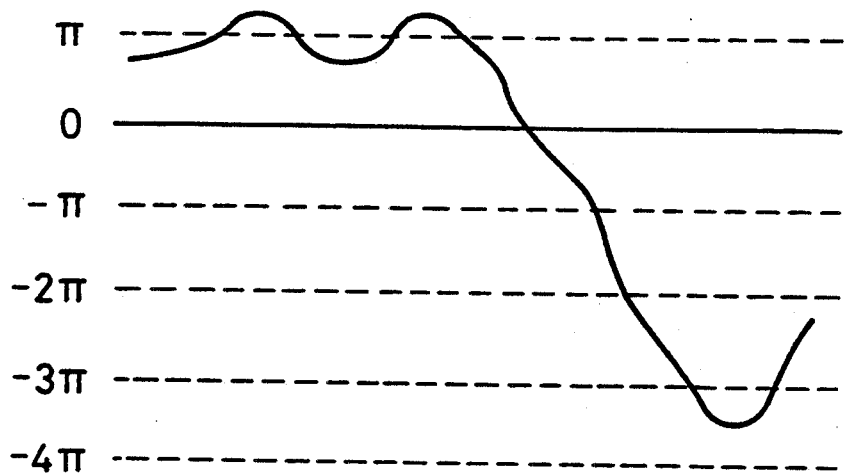

Then, to determine bias values, a comparison is made between the calculation results shown in FIG. 15 and a threshold level "$\alpha$". That is, based on the following inequality (7), assuming now that the threshold level "$\alpha$" is selected to be $1.9\pi$, a bias value of $\pm 2\pi$ is given to the phase difference $\Delta\phi \geq 1.9\pi$; bias value of $+2\pi$ is given to the phase difference $\Delta\phi < 0$ (namely "negative") and a bias value of $-2\pi$ is given to the phase difference $\Delta\phi > 0$ (namely "positive"). It should be noted that this comparison is performed under such a condition that the phase difference $\Delta\phi$ between the adjusting signals is smaller than the threshold level "$\alpha$" except for the discontinuity point "f", and also the values denoted in the parenthesis of FIG. 14 represent the finally given bias values with respect to the starting point "$f_{10}$". When such bias values are given to the phase data shown in FIG. 13, the continuous phase data where no discontinuity point "f" is present at a certain time instant can be obtained as represented in FIG. 15.

Figure 16:
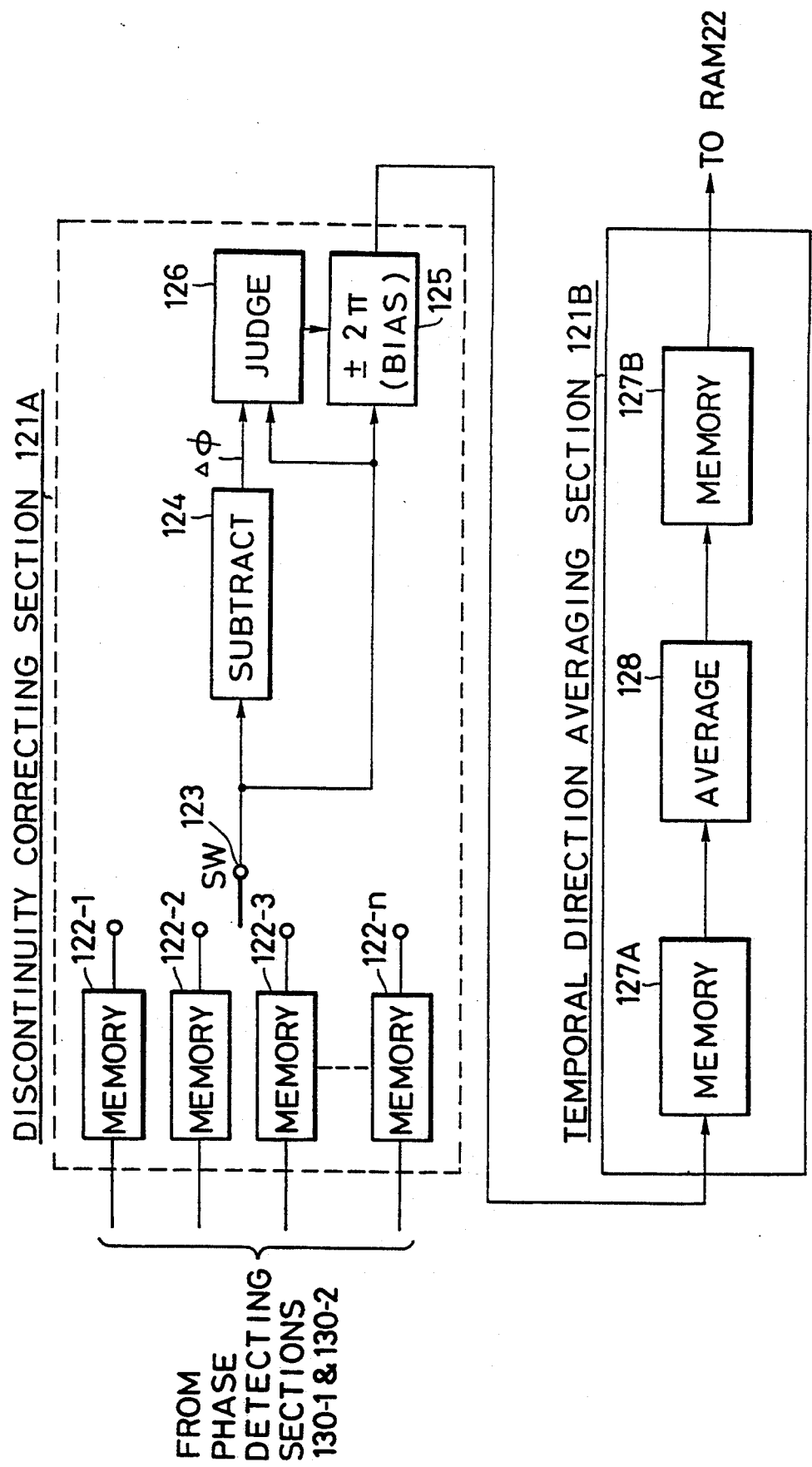
FIG. 16 is a schematic block diagram for showing internal diagrams of the discontinuity correcting section 121A and a temporal direction averaging section 121B represented in FIG. 9.

FIG. 16 is a schematic block diagram for showing an internal arrangement of the discontinuity correcting section 121A and temporal direction averaging section 121B.

In the discontinuity correcting section 121A, the phase data are supplied from the phase detecting sections 130-1 and 130-2 and stored in corresponding memories 122-1 through 122-n. These phase data stored in the memories 122-1 to 122-n are selectively and successively read and supplied to both a subtracter 124 and a bias applying circuit 125 by operating a switch 123. The subtracter 124 successively subtracts the phase data on the adjacent echo signals from each other to obtain the phase differences $\Delta\phi$. The resultant phase differences $\Delta\phi$ are supplied to a bias judging circuit 126. The bias judging circuit 126 judges the phase data based upon the phase difference data $\Delta\phi$ and the threshold value "$\alpha$" so as to determine a proper bias value. As a result of this judgement, the bias applying circuit 125 applies the proper bias value such as $+2\pi$ to the phase data, whereby the discontinuity point contained in this phase data can be corrected, resulting in the continuous phase data.

Then, the continuous phase data are successively obtained from the discontinuity correcting section 121A and thereafter furnished to a first memory 127A of the temporal direction averaging section 121B. A plurality of continuous phase data are averaged in an averaging circuit 128 thereby to obtain the final continuous phase data from which the discontinuities have been eliminated (see FIG. 15).

With the above-described arrangements, especially the discontinuity correcting section 121A and temporal direction averaging section 121B, the second ultrasonic diagnostic apparatus 2000 has such a particular advantage that even when the phase data outputted from the phase detecting section 180 contains the discontinuities "f", the discontinuities can be surely corrected by the phase correcting section 121, in addition to the previous advantages of the first ultrasonic diagnostic apparatus 1000. As a consequence, there is less calculation error caused by the discontinuities contained in the phase data. Since the focal point of the ultrasonic pulses can be formed without any phase shifts contained therein, the ultrasonic images of the biological body with the better image quality can be stably obtained.

ARRANGEMENT OF THIRD ULTRASONIC DIAGNOSTIC APPARATUS

Figure 17:
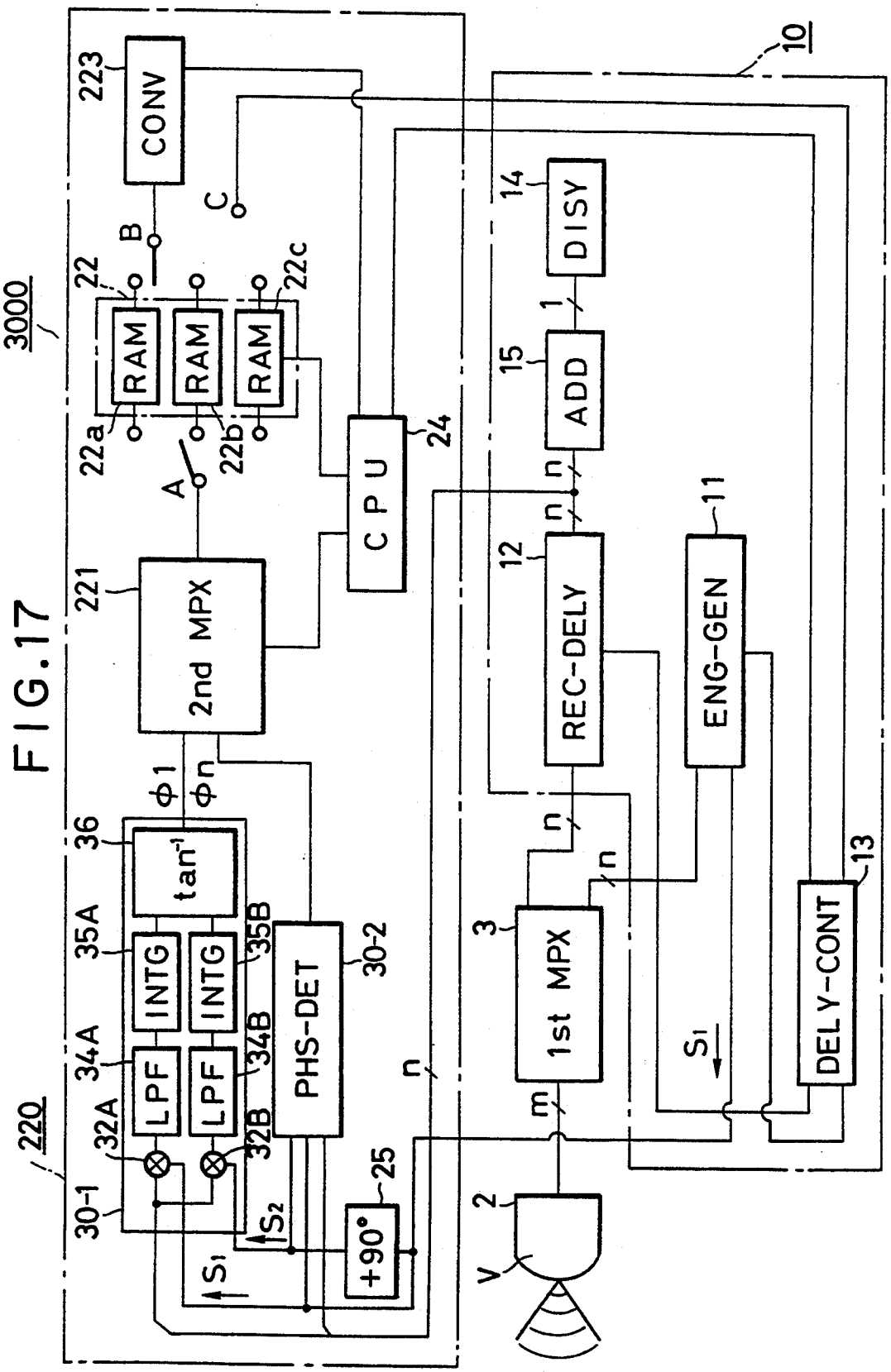
FIG. 17 is a schematic block diagram for representing an arrangement of an ultrasonic diagnostic apparatus 3000 according to a third preferred embodiment of the present invention.

Referring now to FIG. 17, an ultrasonic diagnostic apparatus 8000 according to a third preferred embodiment of the present invention, which is accomplished based on the first basic idea, will be described.

As apparent from FIGS. 5 and 17, the third ultrasonic diagnostic apparatus 3000 employs only a different circuit element, as compared with the first ultrasonic diagnostic apparatus 1000. That is, a second multiplexer 221 and a converting section 223 are newly employed.

The second multiplexer 221 successively transfers the phase data $\phi_1$ to $\phi_n$ outputted from the phase detecting sections 30-1 and 30-2, via the switch to the storage section 22 under control of CPU 24.

The converting section 225 owns the similar function to the phase correcting section 121 of the second ultrasonic diagnostic apparatus 2000 shown in FIG. 9. That is, this converting section 223 performs such a phase correcting process similar to that of the phase correcting section 121; such a converting process that the phase data acquired for all rasters or every several rasters are converted into delay time data; and also such a delay time data interpolation that the data interpolation is performed for the delay time data on the skipped several rasters while the phase data are acquired every several rasters.

With the above-described arrangements, the third ultrasonic diagnostic apparatus 3000 has the similar effects and advantages as those of the second ultrasonic diagnostic apparatus 2000.

SECOND BASIC IDEA

A second basic idea of the present invention will now be described. That is, a quadrature phase detecting means is employed to phase-detect in quadrature echo (reflection) signals obtained from the adjoining transducer elements, so that both an in-phase signal component between the phase-detected echo signals, and also a quadrature signal component are obtained. Furthermore, a phase difference detecting means is employed to obtain a phase difference between these in phase component and quadrature component. As a result, the distortion of the propagation times for the echo signals, which is caused by unequalities of sound velocities within a biological body, is extracted and then corrected, whereby ultrasonic images with improved image qualities may be acquired.

ARRANGEMENT OF FOURTH ULTRASONIC DIAGNOSTIC APPARATUS

Figure 18:
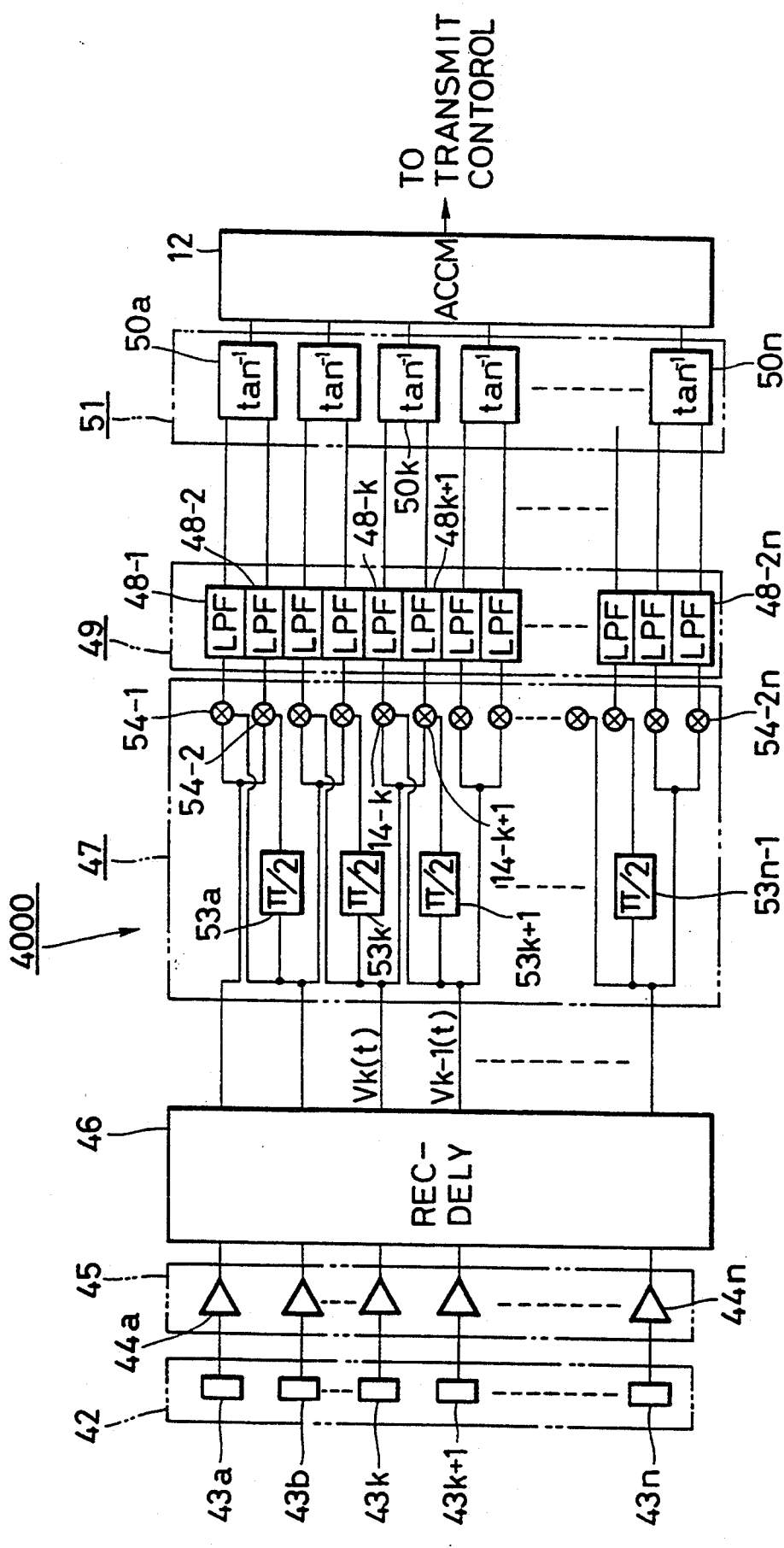
FIG. 18 is a schematic block diagram for showing an arrangement of an ultrasonic diagnostic apparatus 4000 according to a fourth preferred embodiment of the present invention.

Referring now to FIG. 18, an ultrasonic diagnostic apparatus 4000 according to a fourth preferred embodiment of the present invention will be described which is accomplished based on the second basic idea.

The fourth ultrasonic diagnostic apparatus 4000 includes an ultrasonic probe 42 having "n" pieces of transducer elements $3a$ to $3n$ ("n" being an integer larger than 2) arranged in the array form; echo signal amplifying unit 45 constructing of "n" pieces of preamplifiers $4a$ to $4n$ which each amplifies echo (reflection) signal derived from the respective transducer elements $3a$ to $3n$; a reception delay circuit 46 for performing delay processes with respect to the output signals from these preamplifiers $4a$ to $4n$; and a quadrature phase detecting unit 47 for phase-detecting in quadrature all of two adjacent echo signals derived from the reception delay circuit 46. For instance, this quadrature phase detecting circuit 47 phase-detects two echo signals derived from the first and second transducer elements $43a$ and $43b$, or two echo signals derived from the k-th and (k+1)-th transducer elements $43k$ and $43k+1$. The fourth ultrasonic diagnostic apparatus 4000 further includes a filter unit 49 having "2n" pieces of low-pass filters 48-1 to 48-2n by which the respective output signals from this quadrature phase detecting unit 47 are filtered with respect to a boundary frequency "$f_o$", namely the signal components lower than this cut-off frequency "$f_o$" are passed therethrough; a phase difference detecting unit 51 constructed of "n" pieces of arc tangent calculation sections $10a$ to $10n$ for obtaining the phase differences between the adjacent filtered signals by way of the arc tangent process; and also an accumulating process unit 52 for accumulating each of the output signals from the phase difference detecting unit 51 so as to obtain a distribution of arrival time differences (phase differences) among these reception signals reflected from a certain portion within the biological body, i.e., ultrasonic echo signals or echo pulses. The resultant phase difference data are supplied to a transmission controlling system (not shown) for the ultrasonic probe 42.

QUADRATURE PHASE DETECTION

The operation of the quadrature phase detecting unit 47 will now be described more in detail.

As shown in FIG. 18, this quadrature phase detecting unit 47 is mainly arranged by (n−1) pieces of quadrature detectors $53a$ to $53n$-1, and also "2n" pieces of multipliers 14-1 to 14-2n. The quadrature detectors $53a$ to $53n$-1 are employed so as to obtain a quadrature component Qk(t) of (k+1)-th output signal (k=1, 2, ..., n−1) from the reception delay circuit 6. The multipliers 14-1 to 14-2n multiply the in-phase component Ik(t) with the quadrature component Qk(t).

OPERATION OF FORTH ULTRASONIC DIAGNOSTIC APPARATUS

For a better understanding of operations of the fourth ultrasonic diagnostic apparatus 4000, a phase difference between reflection (echo) signals obtained from adjoining two channels, i.e., adjacent transducer elements) will now be detected. For example, the phase difference is calculated between the reflection signal from k-th transducer element $43k$ and the reflection signal from (k+1)-th transducer element $43k+1$ in this preferred embodiment.

Assuming now that the reflection (echo) signal derived from the k-th transducer element $43k$ is expressed by Vk(t), and this reflection signal Vk(t) is expressed by the following equation (7) as a product made of a certain envelope function Ck(t) and a carrier signal of an angular frequency $\omega_o$ ($\omega_o = 2\pi f_o$):

$$Vk(t) = Ck(t) \cdot \cos(\omega_o t + \phi k) \qquad (7)$$

where symbol $\phi k$ is a phase component caused by the arrival time of the reflection signal Vk(t).

Subsequently, the reflection signals Vk(t) and Vk+1(t) are separately amplified by the respective preamplifiers $44k$ and $44k+1$, then are processed by the reception delay circuit 46, and thereafter are supplied to the quadrature phase detecting unit 47. The reflection signal Vk(t) is inputted into the k-th multiplier 54-k and also the (k+1)th multiplier 54-(th).

Also, the (k−1)-th reflection signal Vk+1(t) is inputted into the k-th multiplier 54-k and the quadrature detector $53k+1$. The quadrature detector $53k+1$ shifts the phase of the reflection signal Vk+1(t) by 90° and the 90°-shifted reflection signal is supplied to the multiplier 54-k+1.

The multiplier 54-k+1 performs the multiplying process in accordance with the below-mentioned equation (8):

$$V_k(t) \cdot V_{k+1}(t) = C_k(t)\cos(\omega_o t + \phi_k) \cdot C_{k+1}(t)\cos(\omega_o t + \phi_{k+1}) \quad (8)$$
$$= 1/2 C_k(t) \cdot C_{k+1}(t) \cdot \{\cos(2\omega_o t + \phi_k + \phi_{k+1}) + \cos(\phi_k - \phi_{k+1})\}$$

On the other hand, the (k+1)-th multiplier 54-(k+1) multiplies the k-th reflection signal Vk(t) by a signal produced by phase-shifting the (k-1)-th reflection signal Vk+1(t) by 90° in accordance with the following formula (9):

$$C_k(t)\cos(\omega_o t + \phi_k) \cdot C_{k+1}(t) \cdot \sin(\omega_o t + \phi_{k+1}) = \quad (9)$$
$$1/2 \cdot C_k(t) \cdot C_{k+1}(t) \{\sin(2\omega_o t + \phi_k + \phi_{k+1}) - \sin(\phi_k - \phi_{k+1})\}$$

Subsequently, the k-th low-pass component of 2 $\omega_o$ (namely, second item of right hand of the equation (8), whereby the in-phase component Ik(t) represented by the following equation (10) is obtained:

$$I_k(t) = \tfrac{1}{2} C_k(t) C_{k+1}(t) \cdot \cos(\phi_k - \phi_{k+1}) \quad (10)$$

Similarly, the (k−1)-th low pass filter 48k+1 eliminates the signal component of 2 $\omega_o$ in the equation (9) (namely, second item of right hand in this equation (9)), whereby the quadrature component Qk(t) is obtained as indicated by the following equation (11):

$$Q_k(t) = -\tfrac{1}{2} C_k(t) \cdot C_{k+1}(t) \cdot \sin(\phi_k - \phi_{k+1}) \quad (11)$$

Since the above-described equations (10) and (11) commonly own the phase component $\phi_k$ of the k-th channel and the phase component $\phi_{k+1}$ of the (k+1)-th channel, a phase difference $\Delta\phi_k$ may be calculated by the k-th arc tangent calculation circuit 50k in accordance with the following equation (12):

$$\Delta\phi_k = \phi_k - \phi_{k+1} \quad (12)$$
$$= \tan^{-1}(-Q_k(t)/I_k(t))$$

Then, since there is such a relationship "$\Delta\tau_k = \Delta\phi_k$" between the phase shift $\Delta\phi_k$ of the reflection signal having the angular frequency "$\omega_o$" and the arrival time difference $\Delta\tau_k$, the arrival time difference $\Delta\tau_k$ may be expressed by:

$$\Delta\tau_k = 1/\omega_o \Delta\phi_k \quad (13)$$
$$= 1/\omega_o \tan^{-1}\{-Q_k(t)/I_k(t)\}$$

When the above-described calculation process is executed with respect to the adjoining reflection signals obtained from the channel k=1 until the channel k=n−1, each of the arrival time differences among the adjacent transducer elements (channels) 43a to 43n may be obtained. Furthermore, when these arrival time differences are accumulated by the accumulating unit 52 based upon the below-mentioned equation (14), a distribution about the arrival times of the respective reflection signals (ultrasonic echo pulses) on the reception apertures of these transducer elements 43a to 43n:

$$T_{k+1} = \sum_{i=1}^{k} \Delta\tau_i + T_1 \quad (14)$$

where k=1 through n−1, and symbol "$T_1$" is constant. That is, $T_{k+1}$ indicates the arrival time to the (k+1)-th transducer element $43_{k+1}$ (k=1 to n−1) under condition that the arrival time $T_1$ of the reflection signal to the first transducer element 43a is a reference time.

There are two reasons why the multiplication (mixing calculation) is performed subsequent to the reception delay process (in the reception delay circuit 46) in this fourth preferred embodiment. The first reason is as follows: since, as represented by the above-described equations (10) and (11), the calculation results can be expressed by the product of the envelope functions for two reflection signals whose phase difference is desired, sufficient detection sensitivities cannot be obtained unless overlapped portions of envelops for two reflection signals become sufficiently large. To correct the difference in the propagation distances of the two adjoining reflection signals obtained from the two adjacent channels, the reflection delay circuit 46 is utilized. The second reason is to mitigate such a problem that a folded phenomenon happens to occur during the phase difference detection by reducing the phase difference between the adjoining reflection signals.

As previously described In detail, according to the fourth ultrasonic diagnostic apparatus 4000, the entire construction thereof may be made very simple, namely the quadrature phase detecting unit, filter unit, phase difference detecting unit and accumulating unit in order to achieve the ultrasonic images with higher image quality.

THIRD BASIC IDEA

In accordance with the third basic idea of the present invention, there is no necessity to measure all of phase differences of reflection (echo) signals which are reflected from a large quantity of focal points within a biological body under medial examination. Moreover, desirable delay time correcting values for these reflection signals can be surely obtained so that ultrasonic images of the biological body with better image qualities can be acquired within a short time.

When ultrasonic beams are transmitted to a specific region within a biological body, continuous reflection (echo) signals are received by the respective transducer elements of the ultrasonic probe.

A first correction value calculating unit is employed so as to measure phase differences of reflection signals reflected from only a limited number of focal points among all of the focal points, and also to calculate delay correction values for transmission/reception delay times based upon the resultant phase differences.

A second correction value calculating unit is further employed so as to obtain delay correction values for the remaining focal points other than the above-described limited number of focal points based on the previous delay correction values calculated by the first correction value calculating unit by interpolating the delay correction values for the focal points adjacent to the previously measured focal points.

Also, a designation/control means is employed in order to designate all of regions in an ultrasonic image, or a certain number of regions which are displayed on a display unit, and also to control the first second correction value calculating units whereby the above-described two delay-time values are obtained.

ARRANGEMENT OF FIFTH ULTRASONIC DIAGNOSTIC APPARATUS

Figure 19:
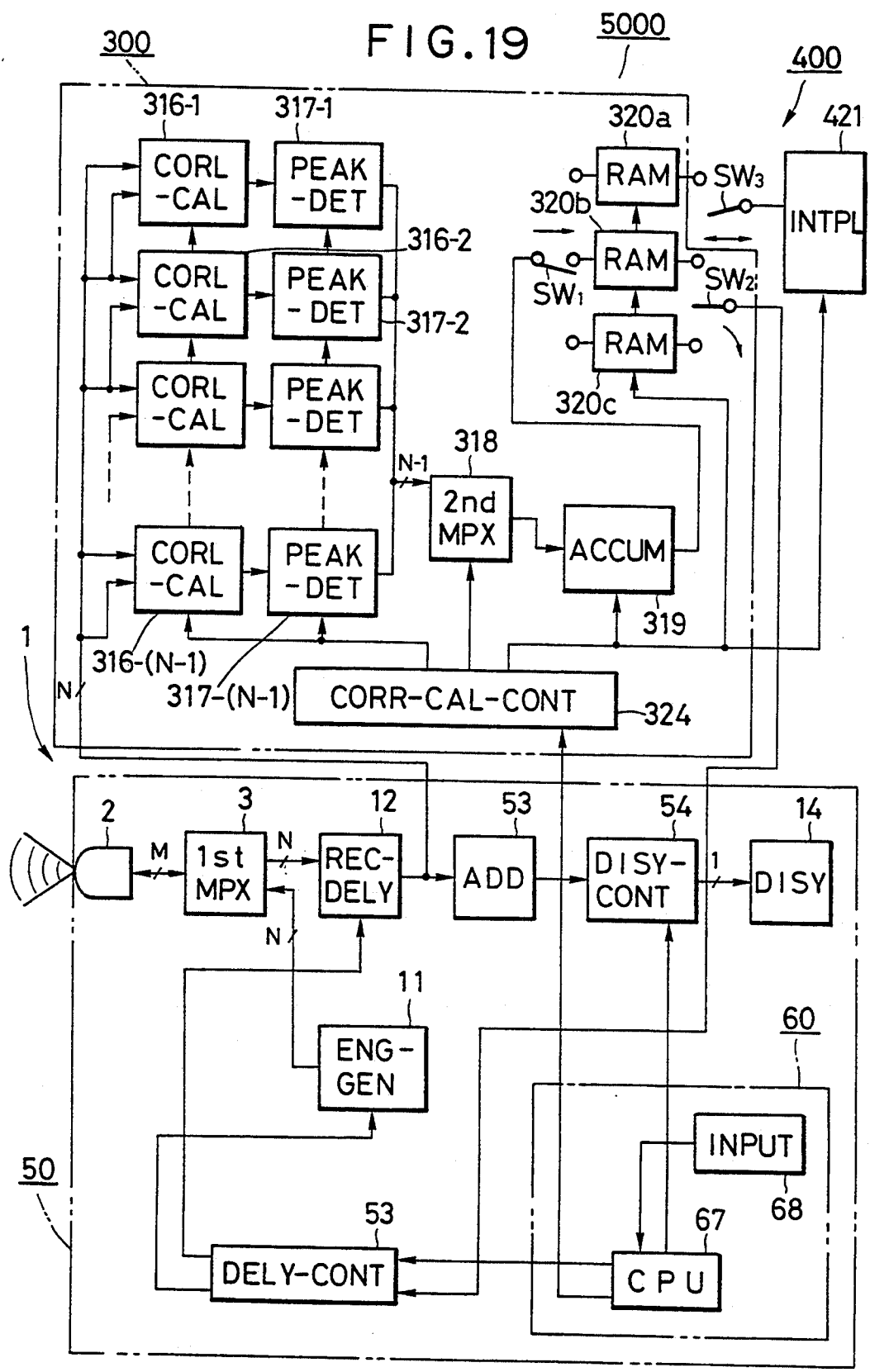
FIG. 19 is a schematic block diagram for illustrating an arrangement of an ultrasonic diagnostic apparatus 5000 according to a fifth preferred embodiment of the present invention.

FIG. 19 represents an overall arrangement of an ultrasonic diagnostic apparatus 5000 according to a fifth preferred embodiment of the present invention, which is accomplished by the third basic idea.

The fifth ultrasonic diagnostic apparatus 5000 mainly comprises a main unit 50; the ultrasonic probe 2 having "m" pieces of transducer elements; a first correction value calculating unit 300 and a second correction value calculating unit 400.

The main body 50 includes the above-explained ultrasonic probe 2; a first multiplexer 3 for switching the transducer elements; a designation/control unit 60 comprising a control processing unit (CPU) 67 and an input unit 68 constructed of a keyboard or track ball; a delay control section 53 for feeding both a transmission control signal and a reception control signal in response to the first and second delay correction values obtained from the first and second correction value calculating units 300 and 400; and an energizing (transmission) signal generating unit 11 for generating a transmission delay-time signal to be supplied to the first multiplexer 6 by receiving the transmission control signal.

The main body 50 further comprises: a reception delay circuit 12 for performing a reception (reflection) signal process based on a predetermined reception delay-time in response to the reception control signal; an adder 53 for adding the results of the reception signal process; and also a display section 14 such as CRT for displaying an ultrasonic image of a biological body under examination under control of a display control section 54.

The function of the designation/control unit 60 is to set a measuring region, a region to be interpolated, a region not to be measured and the like by utilizing the input section 68 and CPU 67.

I. FIRST CORRECTION VALUE CALCULATING UNIT 300

As apparent from FIG. 19, the first correction value calculating unit 300 is constructed of (N-1) pieces of correlation calculating sections 316-1 to 316-(N-1) and (N-1) pieces of peak detecting sections 317-1 to 317-(N-1). The function of the correlation calculating section 316 is to accept the reflection (echo) signals which have been delay-processed in the reception delay circuit 12, to temporally limit the echo signals from the region to be measured (normally this measuring region is coincident with a focal point of ultrasonic transmission pulses) which are received from the adjacent transducer elements, and finally to correlate two sets of temporally limited signals. The function of the peak detecting section 317 is to calculate a phase difference between the adjacent reflection signals from these peak values thereof based upon the correlated value.

This first correction value calculating unit 400 further comprises: a second multiplexer 318 for switching the output signals derived from these peak detecting units 317-1 to 317-(N-1); an accumulating unit 319 for accumulating the output signals from the second multiplexer 318 to obtain first delay correction values; first to third memories 320a to 320c for storing therein the accumulated results (i.e., first delay correction values); a first switch "SW$_1$" provided inbetween the first accumulating unit 319 and the first to third memories 320a to 320c; a second switch "SW$_2$" employed inbetween these memories 320a to 320c and the delay control section 53; a correction value calculation control section 421 for controlling the correlation calculating sections 316-1 to 316-(N-1), the peak detecting sections 317-1 to 317-(N-1), and also the second multiplexer 318, the accumulating circuit 319 and the first to third memories 320a to 320c.

It should be noted that symbol "N" implies a quantity of transducer elements which are driven at the same time for the scanning purpose. For example, in case of the sector scanning operation, "N" is equal to "M".

II. SECOND CORRECTION VALUE CALCULATING UNIT 400

The second correction value calculating unit 400 includes a third switch "SW$_3$" for switching the output data from the first and second memories 320a and 320b; and also an interpolation processing circuit 421. In accordance with the interpolation processing circuit 421, based on the first delay correction values which have been calculated by the first correction value calculating unit 300 and stored in the first and second memories 320a, 320b, a second delay correction value with respect to the remaining focus points is obtained by way of the internal interpolation method or outer interpolation method.

OPERATIONS OF FIFTH ULTRASONIC DIAGNOSTIC APPARATUS

I. FOCAL POINTS IN SECTOR SCANNING OPERATION

Figure 20:
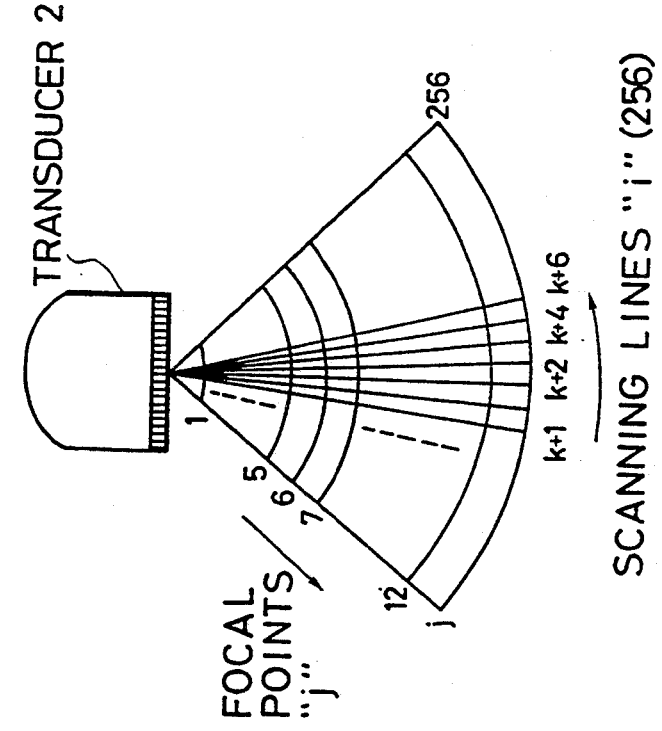

FIG. 20 represents positions of focal points within a specific region of a biological body under medical examination (not shown) in the sector scanning operation by the probe 2. That is, when a tomographic image of this specific region is formed, several hundreds (e.g., 256) of scanning lines and ten to several tens of focal points are set in the fifth ultrasonic diagnostic apparatus 5000.

II. DELAY CORRECTION VALUES/INTERPOLATION

Figure 21:
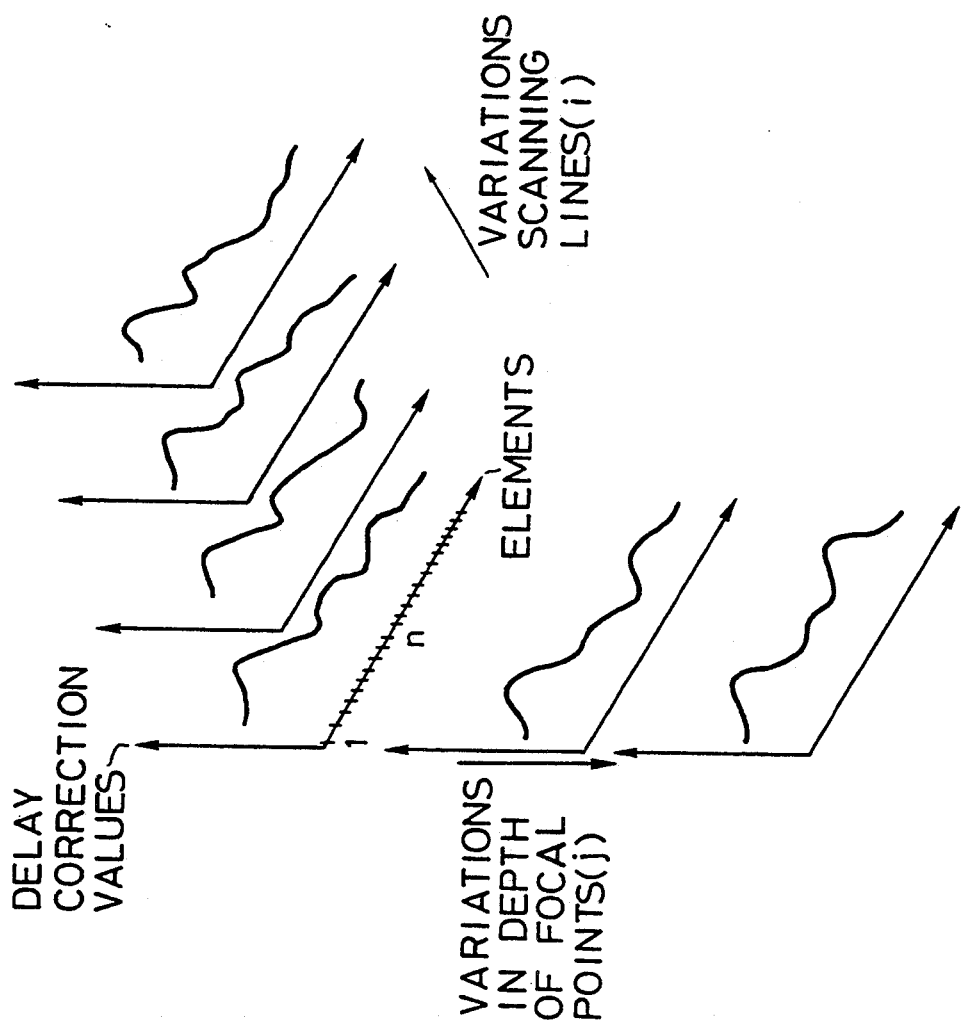
FIGS. 20 to 34 are pictorial explanations of operations and display states for the fifth ultrasonic diagnostic apparatus 5000.

FIG. 21 represents delay correction values required for correcting all of the focal points contained in the tomographic image. The delay correction values imply components of cubic (three-dimensional) matrix which may be expressed as D(n, i, J). Note that symbol "n" indicates the number of transducer elements, symbol "i" denotes the number of scanning lines, and symbol "j" represents the number of focal points.

Figure 22:
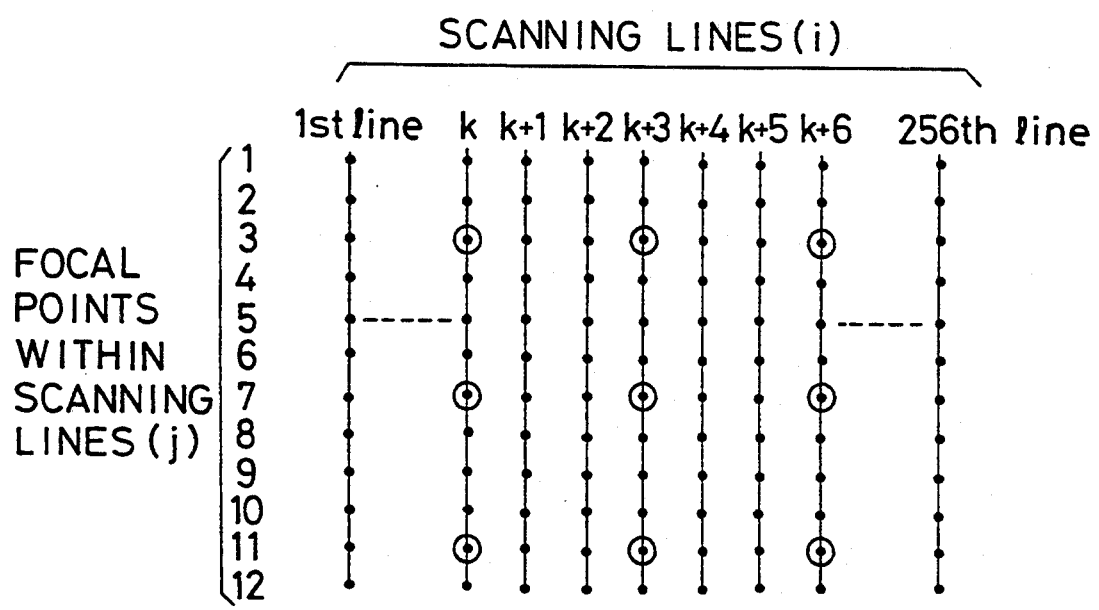

FIG. 22 illustrates how to obtain a delay correction value by way of the interpolation method when the ultrasonic pulses are focused onto (i,J)-th focal point of n-th transducer element. In this case, the second (final) delay correction value D(n, i, J) may be expressed by the following equation (15):

$$D(n,i,j) = \sum_{\alpha=\alpha1}^{\alpha2} \sum_{\beta=\beta1}^{\beta2} H(\alpha L - i, \beta K - j) \cdot \qquad (15)$$

-continued $$S(n, \alpha L, \beta K)$$

In this equation (15), symbol "L" represents an internal of the scanning lines to be measured; symbol "K" denotes each of intervals among the focal points along a depth direction of the measurement; symbol "S" is a first delay correction value obtained from the first correction value calculating unit 300; and symbol "H" denotes a function used to correct the first delay correction value "S" so as to obtain the final (second) delay correction value D.

Also, symbols "$\alpha$" and "$\beta$" represent variables (natural number) indicative of coordinates Cn, $\alpha$L, $\beta$K) for a scanning line changing direction of the first delay correction values "S" and a depth direction of the focal points; symbols $\alpha_1$, $\alpha_2$, $\beta_1$, $\beta_2$ represent samples used for the interpolation calculation in a 1-J plane of the coordinate (n, i, J) of a specific focal point, namely values used for indicating a range of the focal points to be measured.

Furthermore, a single round represents a focal point whereas a double round indicates a focal point at which a first correction value is obtained by the first correction value calculating unit 300.

Figure 23:
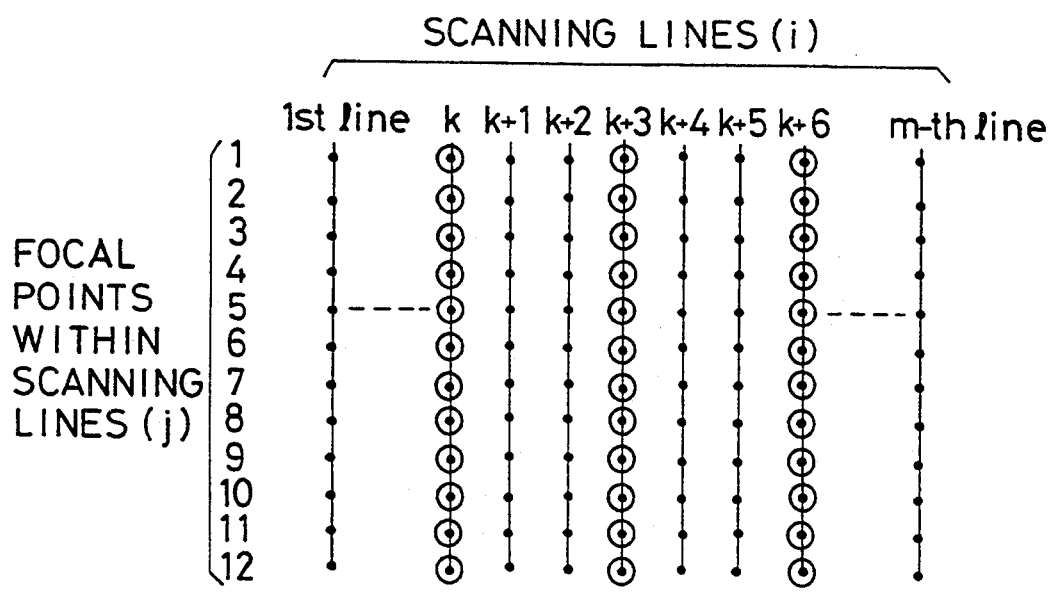

For example, FIG. 23 represents such a case that a delay correction value distribution with respective to n-th transducer element along the scanning line direction is obtained. In this case, the second (desirable) delay correction value D (n, i, J) may be expressed by the below-mentioned equation (16):

$$D(n,i,j) = \sum_{\alpha=\alpha 1}^{\alpha 2} H_1(\alpha L - i) S(n, \alpha L, j) \quad (16)$$

Figure 24:
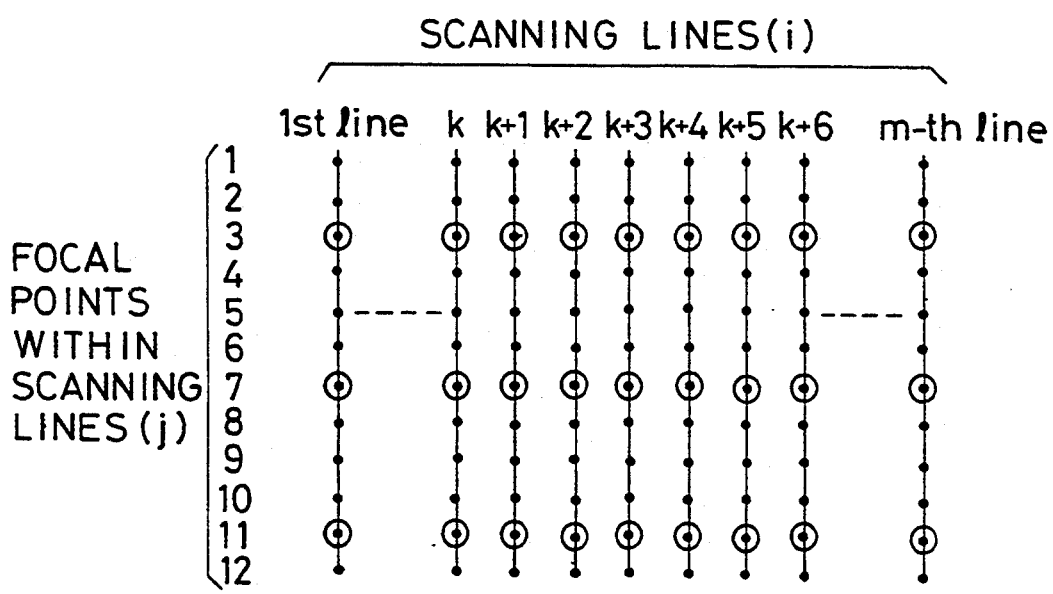

In addition, FIG. 24 represents such a case where a delay correction distribution with respect to the n-th transducer element along the depth direction is obtained.

In this case, a desirable delay correction value D (n, i, J) may be expressed by the following equation (17):

$$D(n,i,j) = \sum_{\beta=\beta 1}^{\beta 2} H_2(\beta K - j) S(n, j, \beta K) \quad (17)$$

Figure 25A:
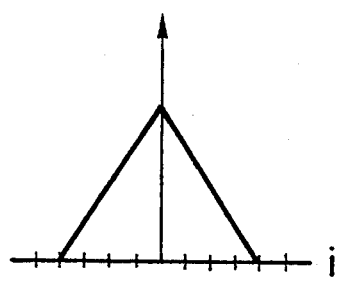
Figure 25B:
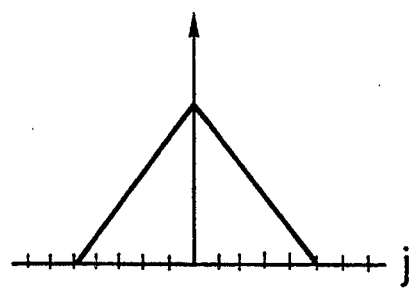

FIGS. 25A and 25B are explanatory diagrams for producing functions $f_1(i, J)$ used to perform the linear interpolation in a generic formula as shown In the above-described equation (15).

Since the function H(i, J) which corresponds to a shown in FIG. 25A and a function H2(J) shown in FIG. 25B, is calculated, a sample used for the Interpolation in a plan (i, J) of a specific focal point may be obtained. In other words, the delay correction values of all focal points at the n-th transducer element can be obtained by way of the so-called "linear interpolation" by employing the values indicative of the range of the measuring focal points. Accordingly, such an interpolation process operation is carried out with respect to all of the transducer elements so that the delay correction values with respect to all of the focal points can be obtained.

It should be noted that the above-described interpolation operations are executed so as to obtain the desirable delay correction values by measuring the phase differences among the reflection from all transducer elements signals with respect to a certain focal point, and alternatively this interpolation processing idea may be applied to the reflection signals among the transducer elements.

That is, the delay correction values may be expressed by the following equation (18):

$$D(n,i,j) = \sum_{\gamma=\gamma 1}^{\gamma 2} \sum_{\alpha=\alpha 1}^{\alpha 2} \sum_{\beta=\beta 1}^{\beta 2} \quad (18)$$

$$H(\gamma J - n, \alpha L - i, \beta K - j) S(\gamma J, \alpha L, \beta K)$$

where symbol "J" indicates an interval of transducer elements to be measured, symbol "$\gamma$" denotes a variable (natural number) representative of the coordinate ($\gamma$J, $\alpha$J, $\beta$J) along an array direction; and also symbols "$\gamma_1$", "$\gamma_2$" represent a sample of the coordinate (n, i, J) at the specific focal point, which is used for the interpolation process operation, namely a value used to indicate the range of the focal point for measurement.

The above equation (18) implies that when there are "K" pieces of transducer elements at the interval "J" and the reflection signals are inputted into the correlation calculating units 316-1 to 316-(N-1) shown in FIG. 19, these reflection signals are derived from, for example, first two adjacent transducer elements and second two adjacent transducer elements which are separated from the first adjacent elements by (K-1) pieces. In other words, no measurement is carried out with respect to the reflection signals derived from (K-1) pieces of transducer elements between the first adjacent elements and second adjacent elements.

In such a case, there is a particular merit that the overall circuit scale of the correlation calculating units 316-1 to 316-(N-1) for measuring the phase differences can be reduced by 1/K.

DISPLAY STATES OF ULTRASONIC TOMOGRAPHIC IMAGES

Both the region designation effected by the designation/control unit 60 and the display states of the ultrasonic tomographic images displayed on the display section 14 will now be described with reference to FIGS. 26 to 34.

To improve precision of the first and second delay correction values calculated by the first and second correction value calculating units 800 and 400, it is required that an object from which ultrasonic pulse beams are reflected should be suitable for the above-described measurement.

Figure 26:
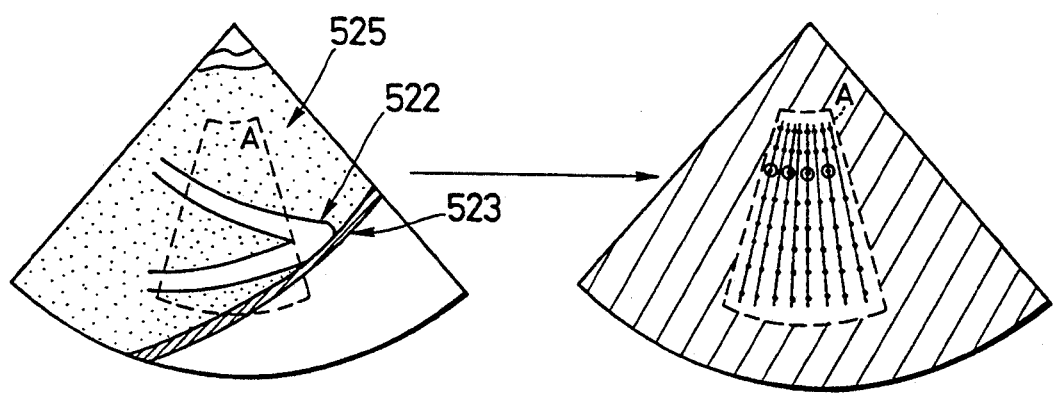
Figure 27:
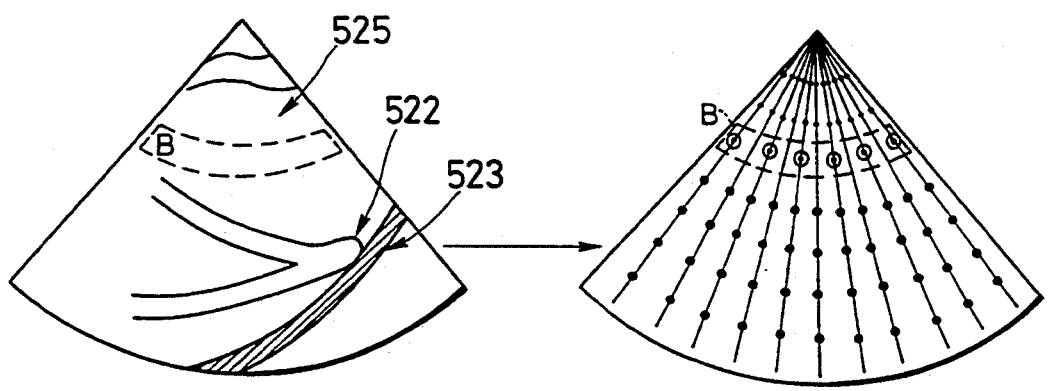

In FIG. 26, there is shown such a case where a region "A" is designated as a region to be interpolated by an operator. Under control of CPU 67, the first correction value calculating unit 800 calculates the first delay correction values of the respective scanning lines at the focal points indicated by two round points within this designated region "A", and also the second correction value calculating unit 400 calculates the second delay correction values at the focal points denoted by a plurality of one round points by way of the Interpolation process. It should be noted that a hatched portion shown in FIG. 26 represents a region where no delay correction is performed; reference numeral 525 indicates an image of a flesh portion of a liver (namely, any liver portions except for blood vessels); reference numeral 522 denotes an image of a blood vessel; and reference numeral 523 represents an image of a diaphragm.

Figure 29:
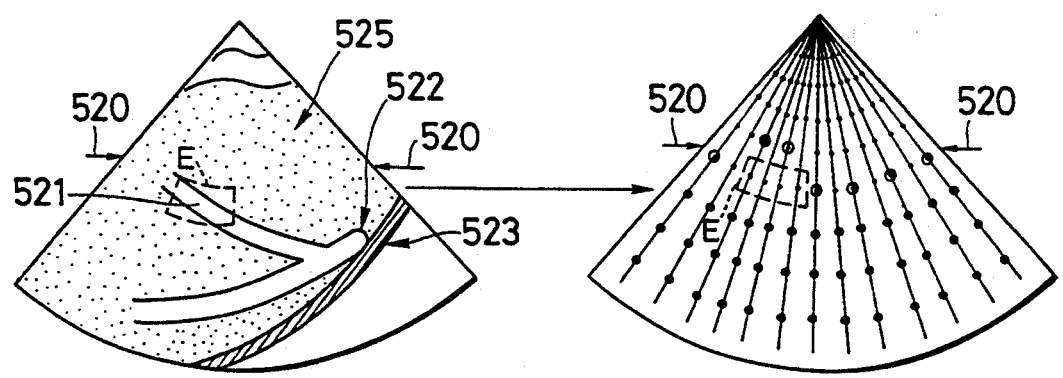

FIG. 29 Indicates such a condition that a region "B" corresponding to the image of the liver's flesh portion 525 on the respective scanning lines is designated as the region to be measured, and only the first delay correction value with respect to the focal points denoted by the two round points, and then the second delay correction values with respect to the remaining focal points are obtained by way of the interpolation process by the second correction value calculating unit 400.

Figure 28:
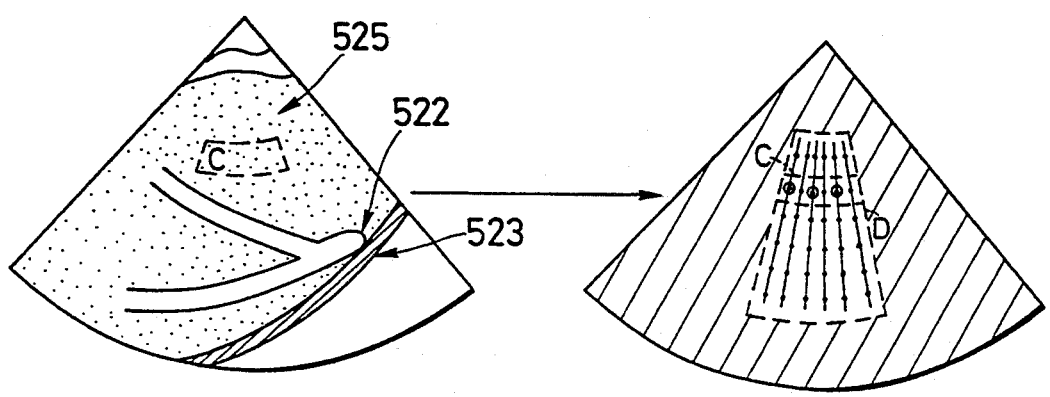

FIG. 28 represents such a case that a relatively small-ranged region "C" corresponding to the image of the liver's flesh portion 525 is designated, and a predictive region "D" containing the small-ranged region "C" is automatically designated under control of CPU 67 and the resultant images are displayed on the display section 14.

Taking account of deterioration in the precision of the desirable (second) delay correction values for the positions separated far from the region "D", which are predictively calculated, it may be Judged that there is a great merit only if the delay correction values for the required portions such as the region "D" of FIG. 28 are obtained.

FIG. 29 represents such a case that an operator instructs via the input unit 68 the fifth ultrasonic diagnostic apparatus 5000 that one region "E" corresponding to the blood vessel's image 522 should not be measured For example, when the region to be measured/connected is displayed on the display section 14 by double arrows 520 under control of CPU 67, if there is such a region as a blood vessel 521 from which no reflection signal is derived within the region denoted by the double arrows 520, the operator designates this non-reflected region as the region "E" not to be measured.

It is of course possible to employ various designating states other than the double-arrow designation.

Figure 30:
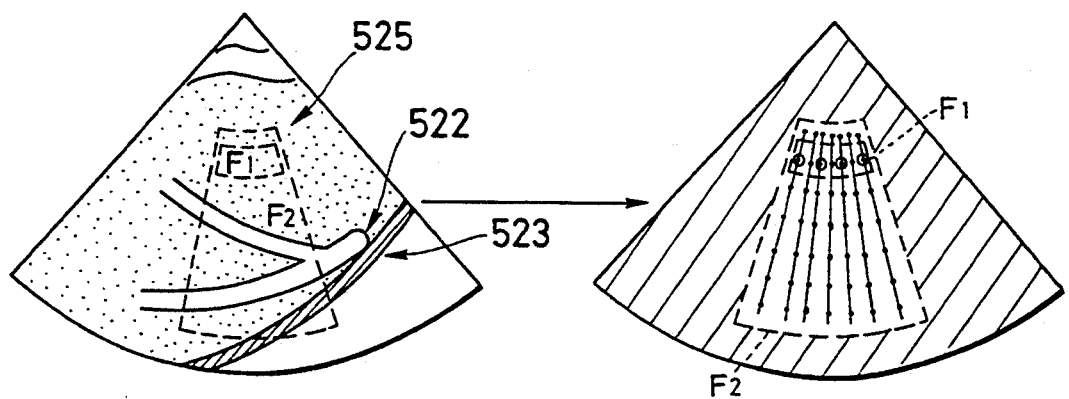

FIG. 30 indicates such a condition that two regions "$F_1$" and "$F_2$" are designated, the first region "$F_1$" denotes a region to be measured and the second region "$F_2$" indicates a region where an interpolation process is required.

Figure 31:
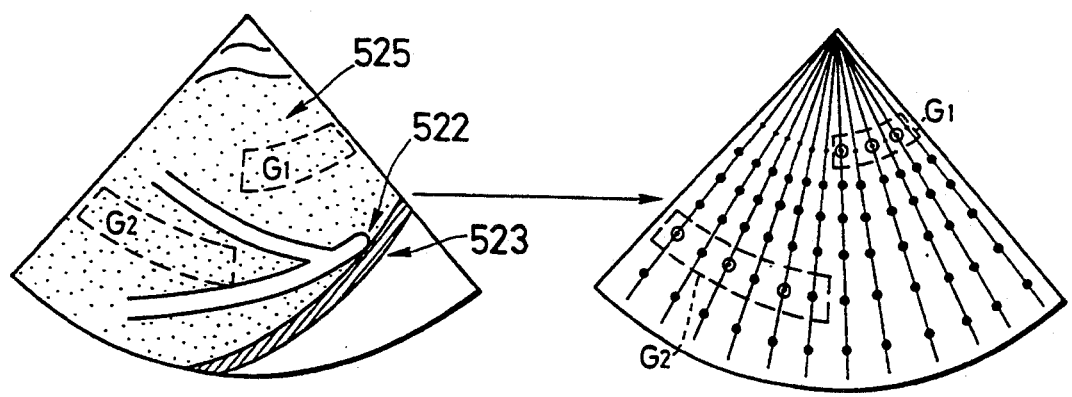
Figure 32:
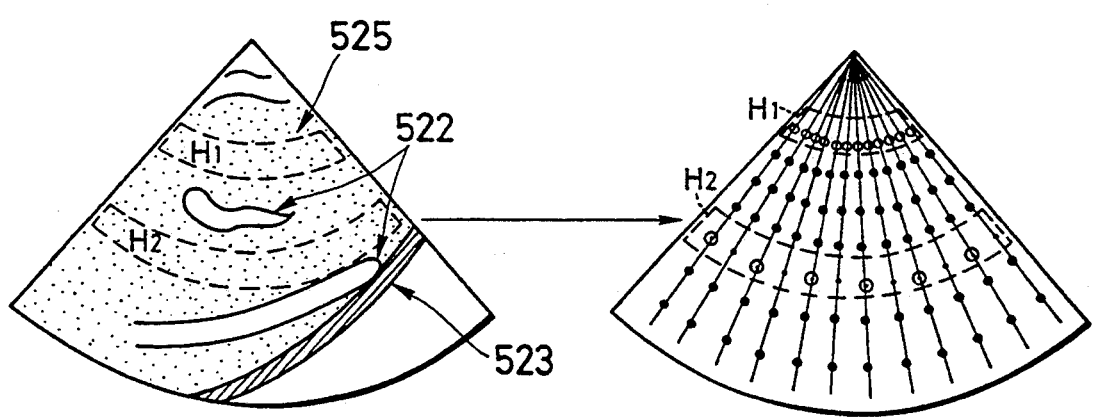
Figure 33:
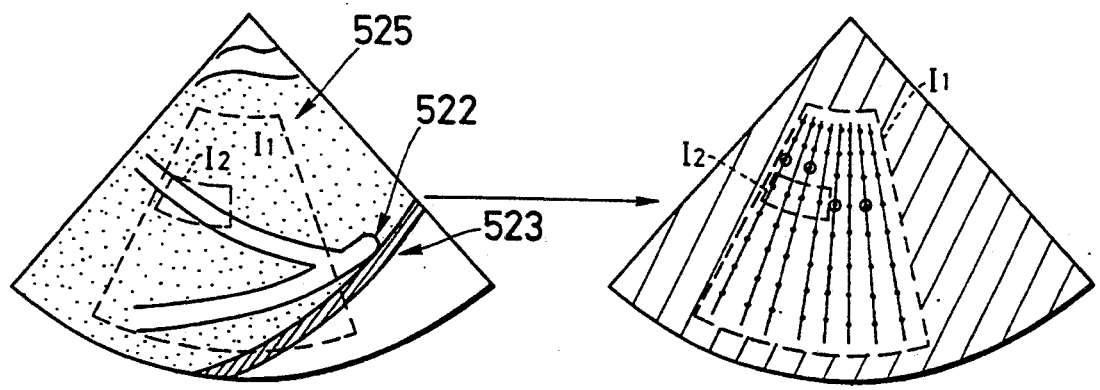

FIGS. 31 and 32 represent the following cases: Two regions $G_1:G_2$ or $H_1:H_2$ are designated and boths are regions to be measured, whereas the remaining regions are used to be interpolated.

It should be noted that the display state of FIG. 31 is suitable for predicting various correction values based on the correction value for one measured focal point on the same scanning line, whereas the display state of FIG. 32 is suitable for predicting the correction values based on the correction values for two measured focal points on the same scanning line.

FIG. 83 illustrates such a case that one region $I_1$ where the predictive correction is performed is designated, and one region $I_2$ not to be measured is also designated.

In this example, there is a particular advantage that the region to be measured may be automatically determined under control of CPU 67 by designating the region "$I_1$", and furthermore if another region not to be measured (e.g., blood vessel 521 of FIG. 29) is present within this region $I_1$ and this region is designated as the region $I_2$, the region to be measured may be automatically removed on the displayed ultrasonic image under control of CPU 67. As a result, the designation efficiency for the regions can be improved.

Figure 34:
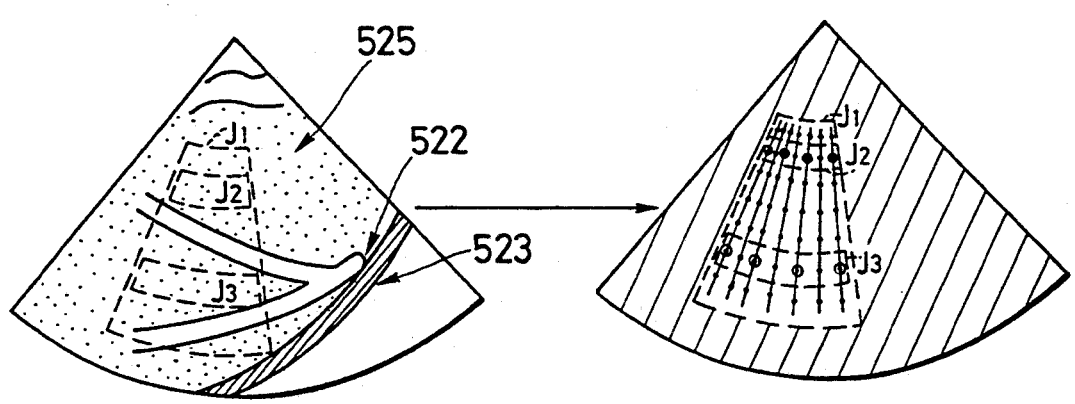

FIG. 34 indicates such a case that three regions $J_1$, $J_2$, and $J_3$ are designated.

The first region "$J_1$" represents a region where the predicative correction should be executed, and the second and third regions "$J_2$", "$J_3$" indicate regions where the ultrasonic measurements should be carried out.

As previously described in detail, according to the fifth ultrasonic diagnostic apparatus 5000, only the first delay correction values for the preselected focal points are obtained by the first correction value calculating unit 300, whereas the second delay correction values for the remaining focal points are obtained by perform the interpolation process on the first delay correction value by the second correction value calculating unit 400. Since the transmission/reception controls of the ultrasonic probe 2 are performed based on the first and second delay correction values, the ultrasonic images of the biological body can be obtained within a short time.

Furthermore, since all regions or only limited number of regions are designated by the designation/control unit 60 and also both the controls for the first and second correction values calculating units 300 and 400 and also the transmission/reception controls for the probe 2 are executed based on these designation results, the ultrasonic tomographic image with respect to the region from which the reflection signals suitable for the measurement is surely derived, can be acquired.

FOURTH BASIC IDEA

As previously described, echo signals reflected from an interior of a biological body under medical examination are necessarily required in order to detect phase distortion contained in ultrasonic pulses. However, since there are portions such as blood vessels from which no echo signals are reflected (will be referred to a "non-echo structure"), there are some possibilities that the phase distortion cannot be detected.

In accordance with a fourth basic idea of the present invention, a histogram of echo signal intensities or strengths is analyzed and then based upon this analysis result, a judgement is made whether or not a correction value for the phase distortion of the ultrasonic pulses is valid. Also, as a result of such a Judgement whether or not any reflecting object is present within a region where the ultrasonic pulses are transmitted and the echo pulses are received, it is Judged whether or not the correction value for the phase distortion is valid. Thus, even if a so-called "non-echo structure" is present within a biological body, the phase distortion of the ultrasonic pulses caused by the inequality of the sound velocity within the body can be corrected.

ARRANGEMENT OF SIXTH ULTRASONIC DIAGNOSTIC APPARATUS

FIG. 85 shows an arrangement of an ultrasonic diagnostic apparatus 6000, according to a sixth preferred embodiment of the present invention, accomplished based on the fourth basic idea.

Figure 35:
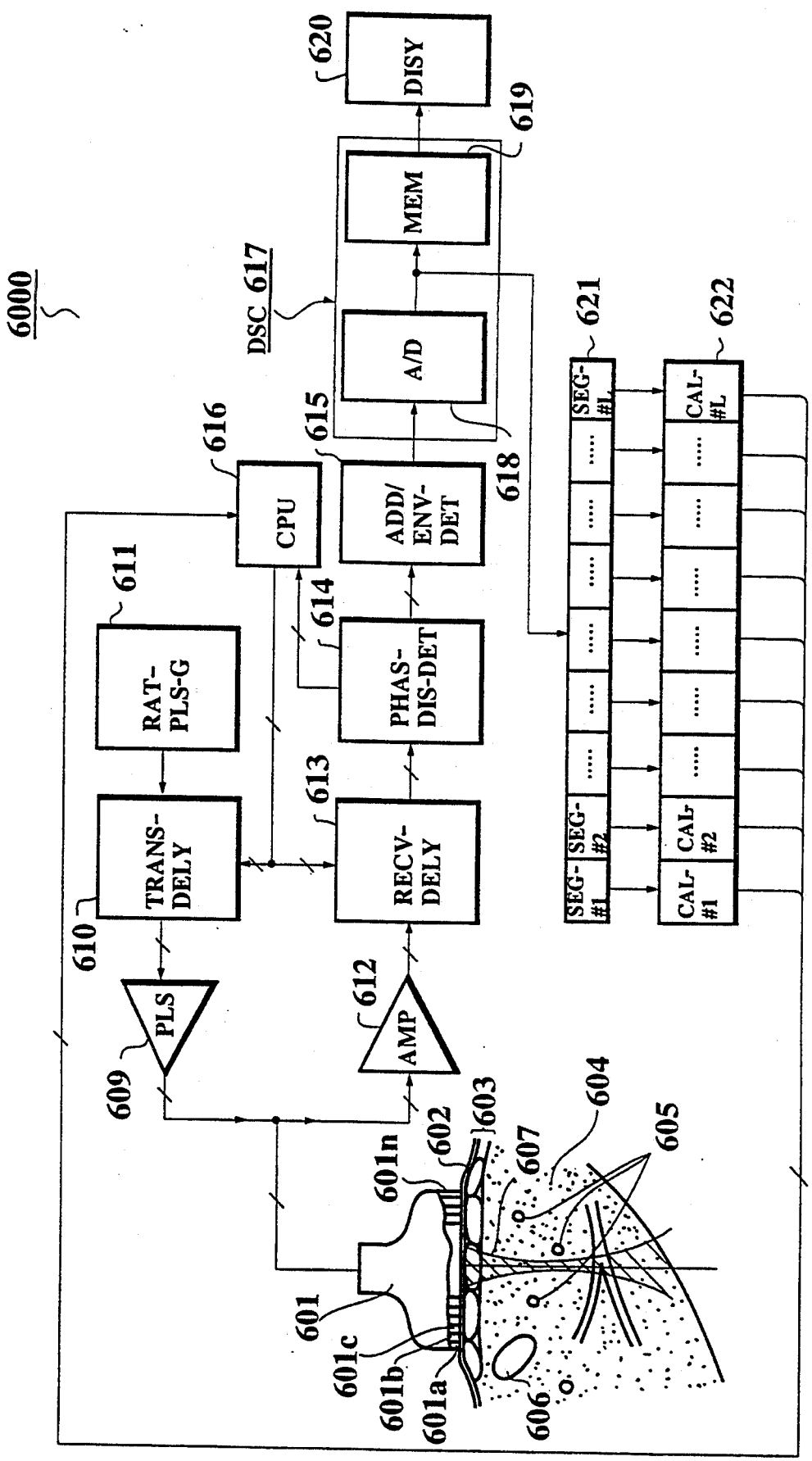
FIG. 35 is a schematic block diagram of an ultrasonic diagnostic apparatus 6000 according to a sixth preferred embodiment of the present invention.

In FIG. 35, reference numeral 601 indicates an ultrasonic probe in which a plenty of transducer elements 601a, 601b, 601c,—601n are arranged in an array form. Reference numeral 602 indicates a biological body under medical examination in which there are an abdomen wall 603, a liver 604, a blood vessel 605 and a cholecystis 606. It should be understood that these blood vessel 605 and cholecystis 606 constitute a so-called "non-echo structure". Reference numeral 607 represents an ultrasonic beam transmitted from the probe 601 which is focused on a predetermined region within the biological body 602. Reference numeral 609 denotes a pulser driven by high voltage pulses; reference numeral 610 is a transmit delay circuit for applying a desirable delay characteristic to the ultrasonic pulse to be transmitted from the probe 601; and reference numeral 611 indicates a rate pulse generator for generating a rate pulse (reference signal).

Also, in FIG. 35, reference numeral 612 indicates a preamplifier for amplifying the ultrasonic echo (reflection) signal received by the probe 601; reference numeral 613 is a reception delay circuit for applying a desirable delay characteristic to the ultrasonic echo signal; and reference numeral 614 denotes a phase distortion detecting circuit for detecting phase distortion from the echo signals. Furthermore, reference numeral 615 indicates an adder/envelope-detector circuit for adding the echo signals with in-phase conditions and for detecting the echo components; reference numeral 616 is a central processing unit (CPU) for controlling an overall control operation of the sixth ultrasonic diagnostic apparatus 6000; reference numeral 617 denotes a digital scan converter (DSC) having an A/D converter 618 and a memory 619, for converting the echo signals into the TV scanning signals, and also reference numeral 620 indicates a display unit for displaying ultrasonic images of the scanned biological body 602.

The sixth ultrasonic diagnostic apparatus 6000 further comprises a 1-line memory 621 for storing therein 1-line data derived from the A/D converter 618, which is arranged by a plurality of segments (SEG-#1, SEG-#2,—, SEG-#L) corresponding to depths of the biological body 602, into which each of the 1-line data is stored; and a calculator 622 having a plurality of calculating sections (CAL-#1, CAL-#2,—, CAL-#L) corresponding to the respective memory segments (SEG-#1, SEG-#2,—, SEG-#L), for analyzing the data stored in the respective memory segments and for supplying the analyzed data to CPU 616. Accordingly, CPU 616 can Judge whether or not the data stored in the respective memory segments (SEG-#1, SEG-#2,—, SEG-#L) are used to correct the phase distortion of the ultrasonic pulses based upon the analyzed data derived from the calculator 622. If CPU 616 makes a decision that the analysis result relating to a certain memory segment is usable to correct the phase distortion, predetermined delay data is set to the transmission delay circuit 610 in such a manner that the ultrasonic pulses may be focused onto the position (depth) of this memory segment. As a consequence, the transmission ultrasonic pulses can be focused onto this focal position by energizing the pulser 609.

OPERATION OF SIXTH ULTRASONIC DIAGNOSTIC APPARATUS

Since the 1-line image data acquiring operation per se is known in this field by utilizing the rate pulse generator 611, pulser 609, adder/envelope-detector 615, DSC 617 and the like, no further detailed explanation thereof is made in this specification. The 1-line (image) data derived from the A/D converter 618 are segmented and stored into the 1-line memory 621, depending upon the lengths corresponding to the depths within the biological body, namely the respective memory segments (SEG-#1 SEG-#2,—, SEG-#L). Thereafter, the data stored is the respective segment memories are analyzed by the calculator 622, the resultant data being supplied to CPU 616.

Then, CPU 616 Judges, based on the analysis results for the respective segment memories (SEG-#1, SEG-#2,—, SEG-#L), whether or not the data stored in the respective segment memories are usable to correct the phase distortion of the ultrasonic pulses. When CPU 616 Judges that the data stored in a certain segment memory can be used, delay time data are set to the transmission delay circuit 610 in order that the transmission focus is coincident with the position of this segment. As a result, the ultrasonic pulses are focused from the probe 601 to this focal position by energizing the pulser 609 under control of the transmission delay circuit 610, and thus the ultrasonic echoes reflected from this focal position are received by the probe 601. The echo signals are produced from the probe 601 and supplied via the preamplifier 612, reception delay circuit 613 to the phase distortion detecting circuit 614 by which the phase distortions contained in the respective transducer elements are detected.

This phase-distortion detection data is supplied either to the transmission delay circuit 610, or the reception delay circuit 613 under control of CPU 616, whereby the detected phase distortions may be corrected since the desirable delay characteristic data are given to the transmission delay circuit 610, and the ultrasonic pulses are again transmitted from the probe 601. Alternatively, after such a delay correction is performed only in the reception delay circuit 613, the echo signals are fed via the adder/envelope-detector 615 to DSC 617 so that the phase-distortion corrected images are finally displayed on the display section 620. It should be noted that the operations from the judgements of the respective segment data to the corrections thereof are added in a serial form to the respective segments.

In such a case that the transmission focal point is fixed and the delay amount correction is performed only for the echo signal reception. There is a particular advantage that although a degree of corrections becomes relatively incomplete, since the required correction can be achieved within a time period of 1 rate (namely, a time period required for detecting 1-line data under such a condition that an ultrasonic pulse is once transmitted toward an inner portion of a biological body at a predetermined depth and echo pulses are reflected therefrom), the phase distortion of the echo signals can be corrected without deteriorating real-time characteristics. To the contrary, when the transmission focal points are coincident with each of the effective segments (i.e., the data stored in these segment memories are usable for correcting the phase distortions), the phase-distortion correction can be realized in perfect conditions though the real time characteristic might be slightly deteriorated.

Furthermore, when it is Judged that the data stored in the segment memories (SEG-#1, SEG-#2,—, SEG-#L) are not used for correcting the phase distortion as a result of judgement, the following correction is carried out. That is, the correction is performed in such a manner that the focal point is coincident with the above-described position (i.e., the position for the segment memories whose data cannot be used for the phase distortion correction) with employment of correction values for the data of the segment memories whose positions are deeper or shallower than the first-mentioned position, and the data stored in these deeper or shallower segment memories can be utilized as the phase distortion corrections. Also, correction values predicted by the above-described correction values may be used.

HISTOGRAM ANALYSIS

A description will now be made of an algorithm to judge whether or not the 1-line data stored in the 1-live memory 621 are used to correct the phase distortions.

Figure 36A:
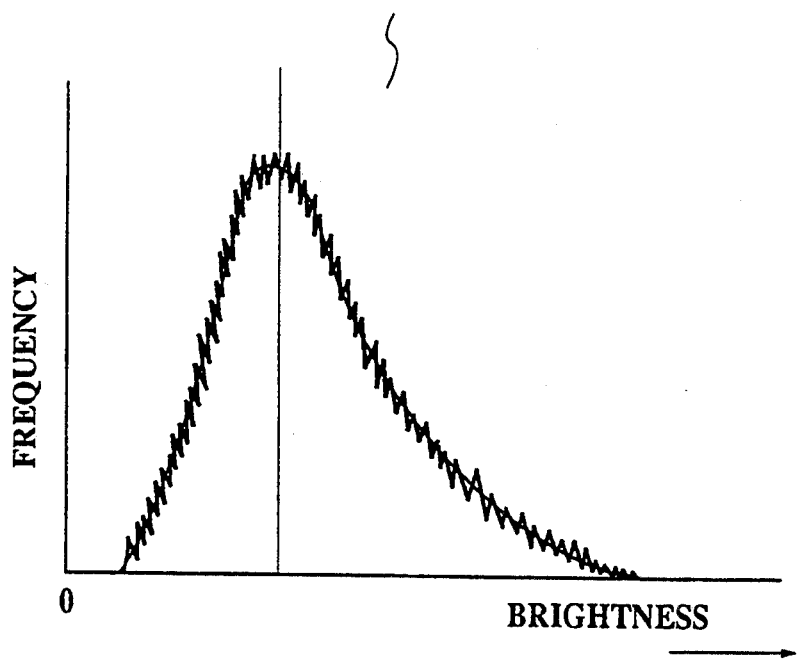
Figure 36B:
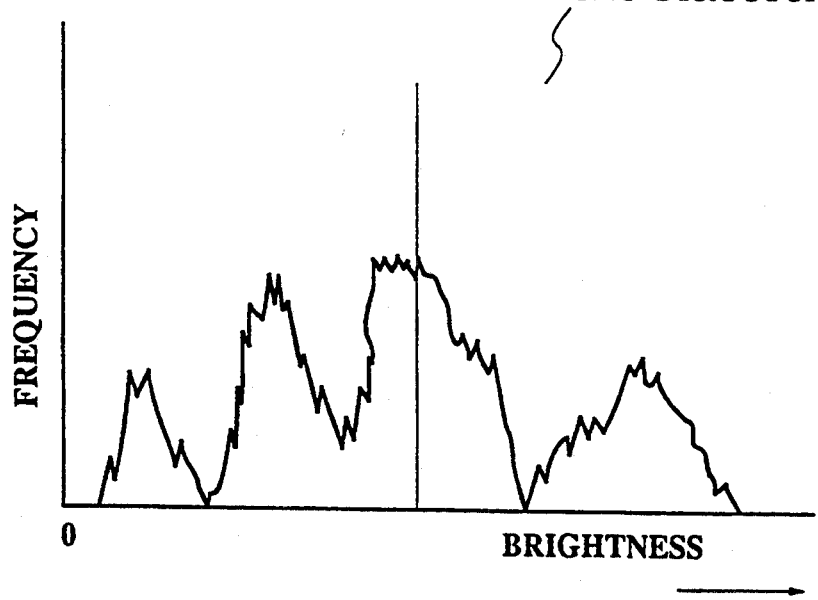

This algorithm may be realized by employing a method for analyzing an echo-signal intensity histogram. More specifically, as represented in FIG. 36A and 36B, the data stored in the respective segment memories (SEG-#1, SEG-2", —, SEG-#L) are used to form graphic representations in which an abscissa indicates a brightness of the respective data and an ordinate indicates a frequency thereof. Based upon patterns shown in these graphic representations, the above-described Judgement can be performed.

This may be considered from such an idea that reflection waves from a speckle region are produced in such a manner that a large quantity of reflection waves from the speckle region are superimposed with each other at random phase relationships, and this speckle region is sufficiently small as compared with the wave lengths of the ultrasonic pulses. Then, it is known that a histogram with respect to such a speckle region becomes a function which is statistically determined (Rayleigh's distribution in this case). As a consequence, it can be easily discriminated the formed histogram from the reflection waves derived from the speckle region (as shown in FIG. 36A), or the reflection waves derived from the non-echo structure (as shown in FIG. 36B), while the parameters for determining the curves of the Rayleigh's distribution (in this case, dispersion values of reflection intensities with respect to the reflectors present within the speckle region) are varied. In other words, by recognizing the patterns of the formed histograms, it can be judged whether the reflection waves are derived from the speckle region (see FIG. 36A) or the non-echo structure (see FIG. 36B).

As seen from FIG. 36B, since the reflection intensities are not produced at random, it is a very complex pattern different from the Raylelgh's distribution.

ARRANGEMENT OF HISTOGRAM FORMING CIRCUIT

Referring now to FIG. 37, a histogram forming circuit 650 will be explained which is employed in the calculator 622 shown in FIG. 35.

In FIG. 37, the image (echo signal) data stored in the 1-line memory 621 is supplied to ROM 652 having an address table. Thus, address data is read out from ROM 652 and thereafter supplied to both a memory 654 and an increment instructing circuit 656. Since an increment instruction is given from the increment instructing circuit 656, the address value is incremented by 1 so that the desirable histogram may be formed.

As previously described in detail, in accordance with the fifth ultrasonic diagnostic apparatus 5000 shown in FIG. 35, the judgement whether or not the data are available in the phase distortion corrections, can be readily performed by the pattern matchings. Also, since there is another possibility to make such a judgement based upon simple comparison between the average value and the dispersion value of the distribution, various Judging bases may be employed, taking account of both the statistical characteristics for the reflection waves and the various factors In this system, for instance, compactness, low cost and high speed.

ARRANGEMENT OF SEVENTH ULTRASONIC DIAGNOSTIC APPARATUS

Figure 38:
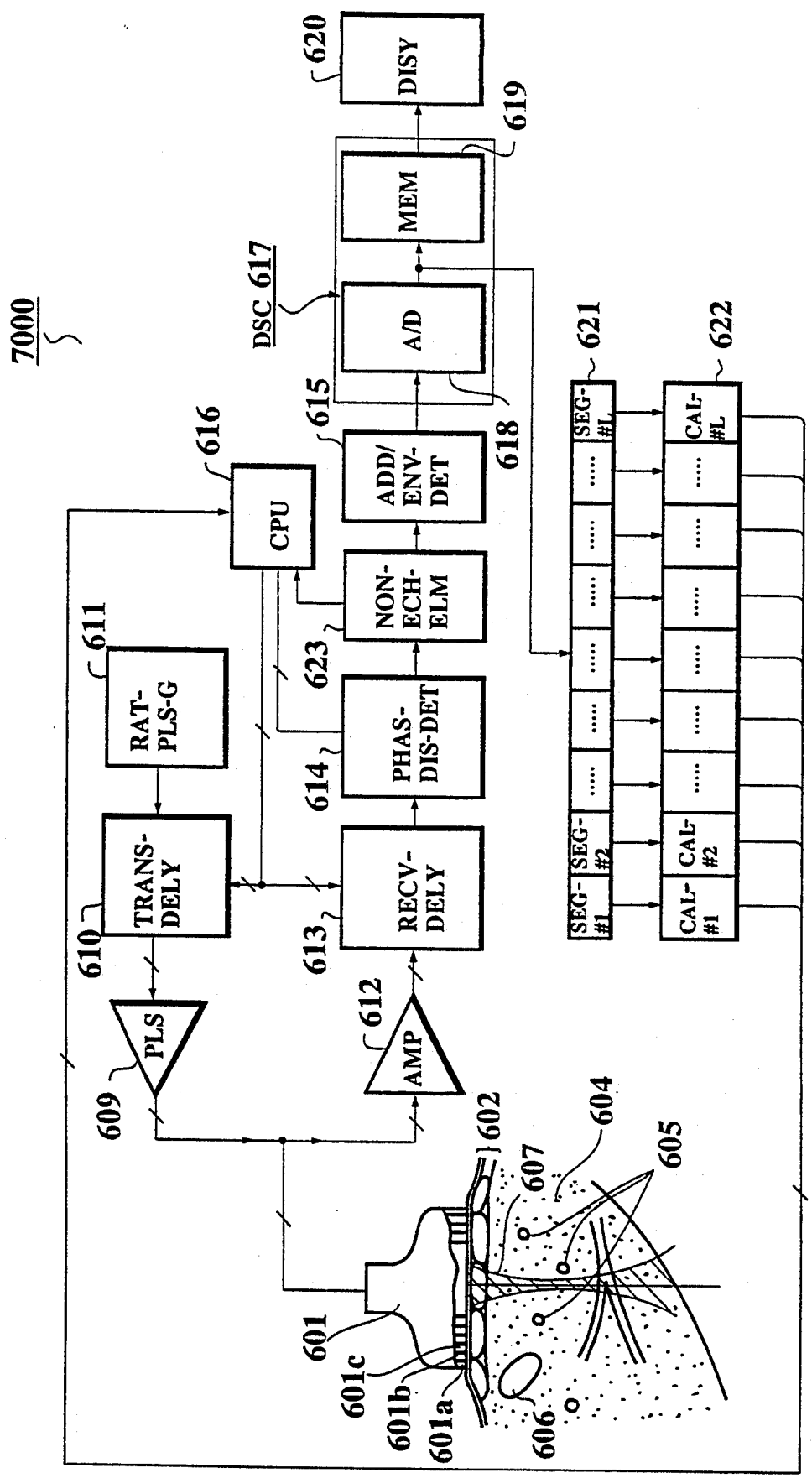
FIG. 38 and 40 represent arrangements and operations of an ultrasonic diagnostic apparatus 7000 according to a seventh preferred embodiment of the present invention.

FIG. 38 represents an ultrasonic diagnostic apparatus 7000 according to a seventh preferred embodiment of the present invention. This seventh ultrasonic diagnostic apparatus 7000 is made by slightly modifying the sixth ultrasonic diagnostic apparatus 6000 shown in FIG. 35, that is, a circuit 623 for eliminating a non-echo structure component is newly interposed between the phase-distortion detecting circuit 614 and the adder/envelope-detector 615.

The feature of this seventh preferred embodiment is such that the Judging basis of this embodiment is relaxed or eased as compared with the previous sixth preferred embodiment, and the Judgement is executed whether or not there is an echo signal. This feature is realized by newly employing the circuit 623 for eliminating the non-echo structure components.

In the seventh ultrasonic diagnostic apparatus 7000, no analysis is performed with respect to the histograms for intensities of echo signals as in the sixth preferred embodiment, but the Judgement is carried out by comparing an averaged value of reflection signals with a certain threshold level "$V_T$". More specifically, when the averaged value of the echo signals exceeds the threshold level "$V_T$", it is judged that the echo signals are regarded to be coincident and also the phase distortion detection is effectively performed. Conversely, if the averaged value does not exceed the threshold level "$V_T$", the phase distortion detection is not effectively carried out.

In accordance with the seventh preferred embodiment, although it may be considered to be effective even when the echo signals reflected from the non-echo structure are contained In the entire echo signals, since such a circuit 623 for eliminating the non-echo structure component is employed, the above-described echo signals from the non-echo structure are eliminated, whereby the averse influences caused by the non-echo structure and given to the phase distortion detection may be eliminated.

PICTORIAL EXPLANATION OF PHASE DISTORTION DETECTION

Figure 39A:
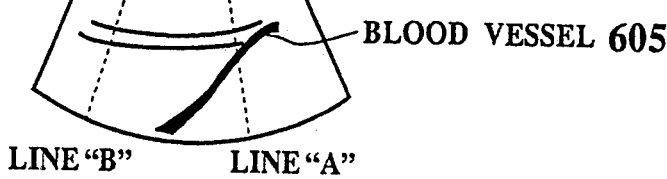
Figure 39B:
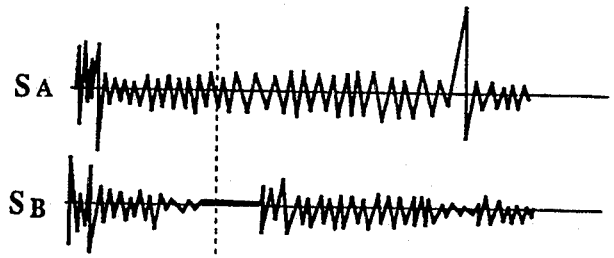
Figure 39C:
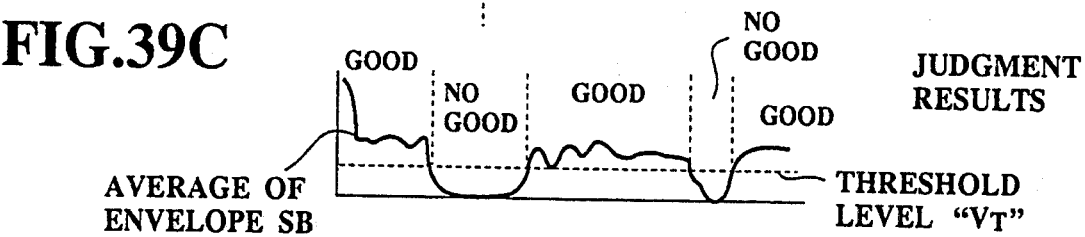

FIGS. 39A to 39C are pictorial explanation of the phase distortion detection effected in the seventh ultrasonic diagnostic apparatus 7000 shown in FIG. 38.

In case of a scanning line "A" of a sector scanning area 700 shown in FIG. 39A, a reflection (echo) signal "$S_A$" having a uniform waveform is obtained from the probe 601, which exceeds the threshold level "$V_T$".

To the contrary, when the sector scanning region 700 is scanned by a scanning line "B" as represented in FIG. 39A, in which cholecystis 606 is located, a reflection signal "$S_B$" having an unequal waveform is obtained from the probe 601, which partially exceeds the threshold level "$V_T$". In this case, it can be Judged that the phase distortion detection is not effective for the correction purpose.

FIG. 39C illustrates how to Judge whether or not the phase distortion detection is effective by comparing the signal levels of the echo signals "$S_B$" with the threshold level "$V_T$". It should be noted that the reflection (echo) signals employed in this preferred embodiment have been processed by, for example, STC means or the like to eliminate adverse influences such as attenuation within the biological body.

Figure 40:
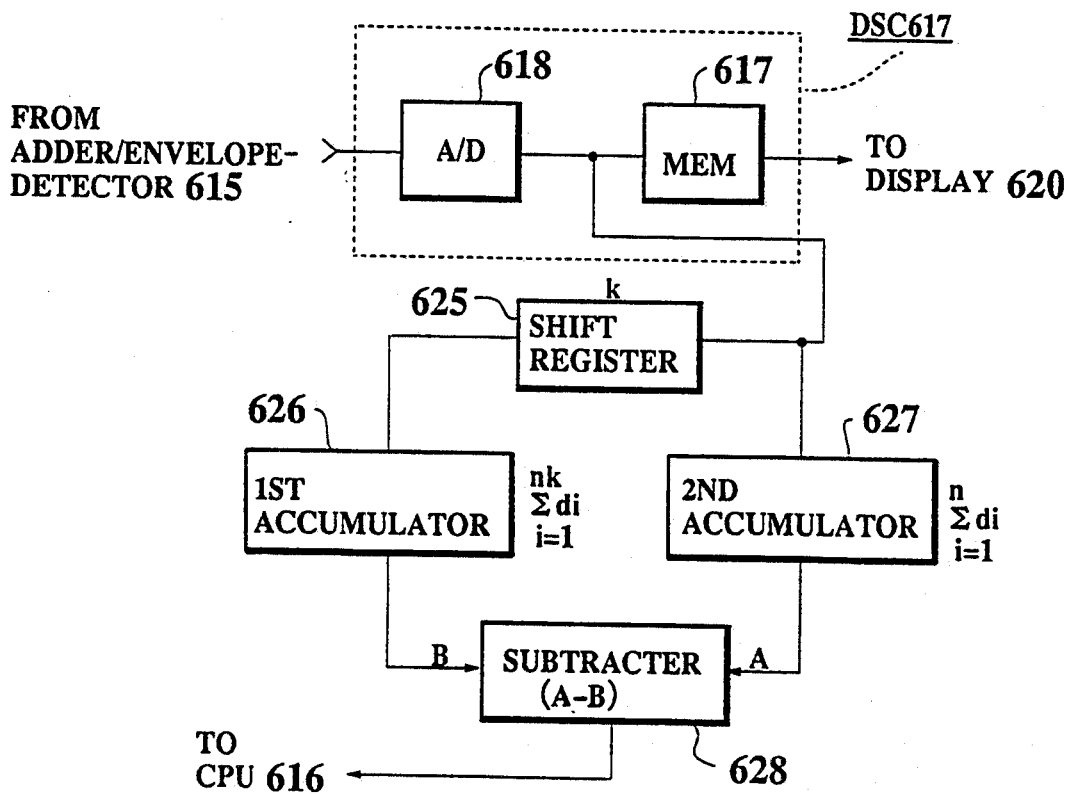

FIG. 40 represents an average value calculating circuit for the reflection signals used in this ultrasonic diagnostic apparatus 7000. This calculating circuit is constructed of a shift register 625, a first accumulator 626, a second accumulator 627 and a subtracter 628. In accordance with the average value calculating circuit. The average values among "K" pieces of samples may be obtained every clock pulses so that a Judgement may be simply achieved whether or not the respective reflection signals are effective.

Furthermore, when a Judgement is made that a certain region is improper with respect to the phase distortion detection, the phase distortion may be corrected with employment of the correction values for the effective regions around the first-mentioned region, or other correction values predicted by these correction values.

FIFTH BASIC IDEA

Even when there is a highly (strongly) reflecting article within a biological body under medical examination, and a distribution of propagation time differences is inclined, a low frequency signal component causing this inclination is eliminated by employing such a process as movement averaging method, so that delay times in the transmission/reception units are controlled.

ARRANGEMENT OF EIGHTH ULTRASONIC DIAGNOSTIC APPARATUS

Figure 41:
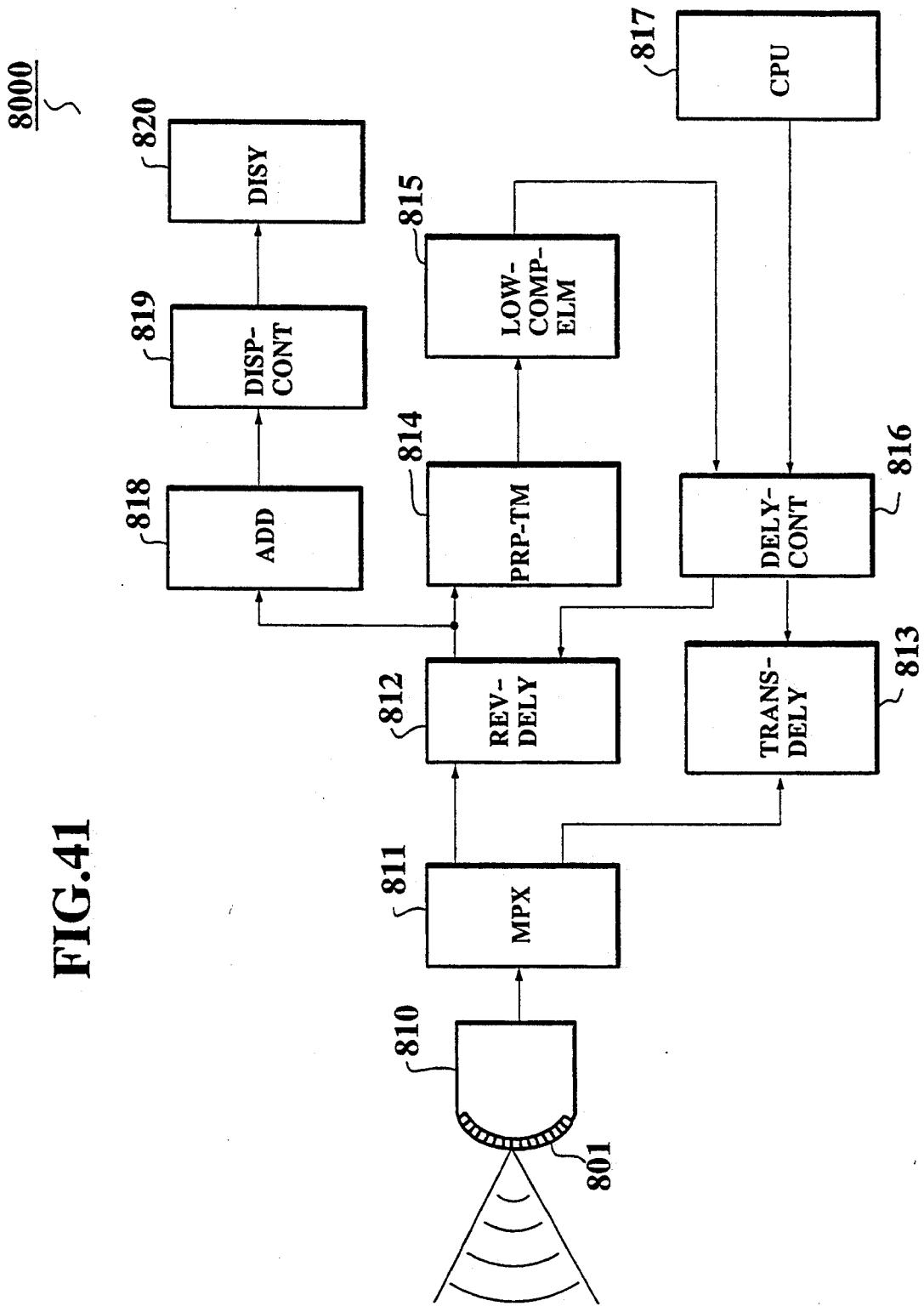
FIGS. 41 to 44 represent arrangements and operations of an ultrasonic diagnostic apparatus 8000 according to an eighth preferred embodiment of the present invention; and, FIGS. 45 and 46 represent an arrangement and operations of an ultrasonic diagnostic apparatus 9000 according to a ninth preferred embodiment of the present invention.

FIG. 41 is an arrangement of an ultrasonic diagnostic apparatus 8000 according to an eighth preferred embodiment of the present Invention, which is accomplished based upon the fifth basic idea.

In FIG. 41, the eighth ultrasonic diagnostic apparatus 8000 is constructed of an ultrasonic probe 810, a multiplexer 811, a reception delay section 812, a transmission delay section 813, a delay control section 816, an adder 818, a central processing unit 817 and a display control section 819 and a TV monitor 819. Since the above-described circuits are known, no further explanation thereof is made. Furthermore, the eighth ultrasonic diagnostic apparatus 8000 further comprises as a featured circuit thereof; a propagation time measuring section 814 and a low-frequency component eliminating section 815.

Figure 42:
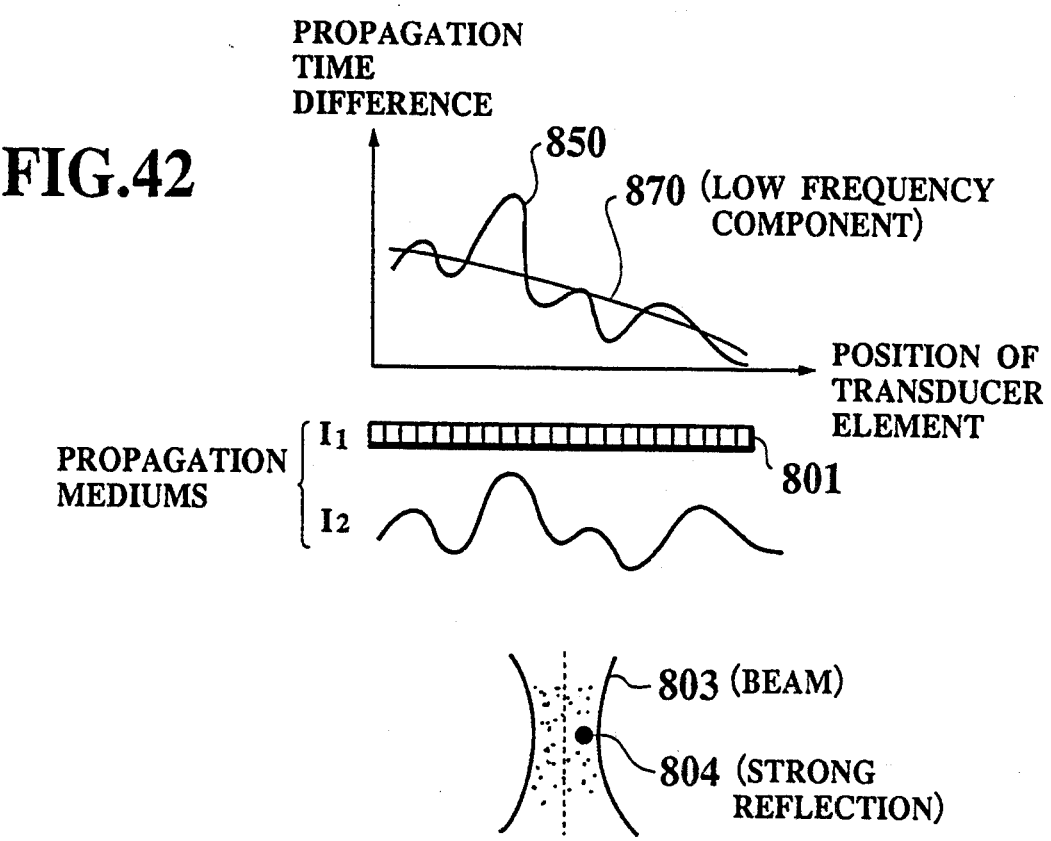

The function of the propagation time measuring section 814 is to receive the reflection signal outputted from the reception delay section 812 in order to measure the propagation time of the reflection signal. As a result, differences in propagation mediums of a biological body (not shown in detail) are obtained as a distribution curve 850 for propagation time differences, as represented in FIG. 42 (will be discussed later).

The low-frequency component eliminating section 815 first obtains a low-frequency component 870 from the distribution curve 850 with employment of the process such as the movement averaging method, secondly eliminates this low-frequency component 870, and thirdly supplies a delay-time correction signal from which the low-frequency component has been eliminated, to the delay control section 816.

Then, the delay control section 816 controls the delay times for the transmission delay section 813 and reception delay section 812 based on the above-described delay-time correction signal from the low-frequency component eliminating section 815 and also the delay time signal from CPU 817.

OPERATION OF EIGHTH ULTRASONIC DIAGNOSTIC APPARATUS

Figure 43:
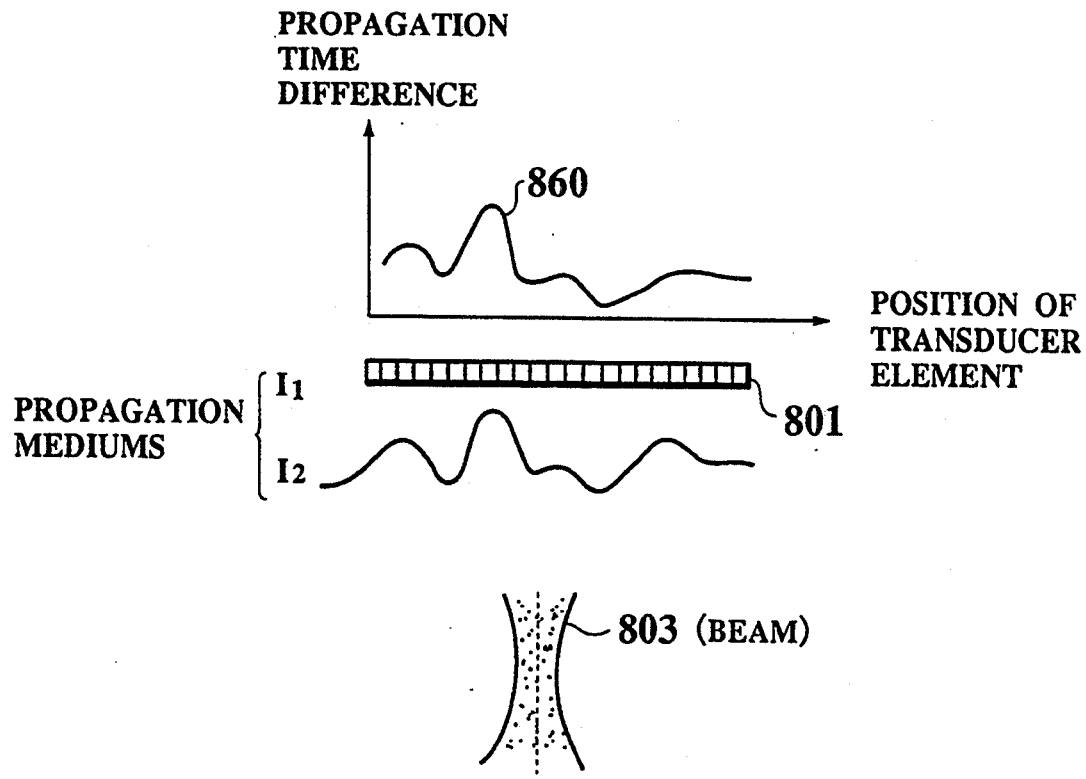

Assuming now that there are different (ultrasonic) propagation mediums "$I_1$" and "$I_2$" such as fat and muscle, but no strong reflecting article (as 804 shown in FIG. 42) in an ultrasonic imaging field by the eighth ultrasonic diagnostic apparatus 8000. The echo (reflection) signals obtained from the transducer elements 801 of the ultrasonic probe 810 are processed in the propagation time measuring section 814 so that a distribution curve 860 for propagation time differences as represented in FIG. 43. This distribution curve 860 indicates a boundary of these difference propagation mediums $I_1$ and $I_2$. Therefore, if the reception delay time is controlled based on this distribution curve 860, the ultrasonic beam 803 can be focused irrelevant to variations in the propagation mediums, whereby an ultrasonic image having better space resolution can be acquired.

On the other hand, as shown in FIG. 42, if a strongly reflecting article 804 is present within the ultrasonic beam 803, or imaging field, since the propagation direction of this beam 803 is disturbed, the resultant distribution curve 850 obtained from the propagation time measuring section 814 is inclined.

Then, in the low-frequency component eliminating section 815, the low frequency component 870 is calculated by way of the movement averaging method based on this distribution curve 850, and also the delay-time correction signal from which this low frequency component has been eliminated is outputted. Subsequently, as previously described, the transmission/reception timings of the ultrasonic (echo) pulses are corrected in the respective transmission delay section 813 and reception delay section 812 based on this delay-time correction signal.

As a consequence, in accordance with the eighth ultrasonic diagnostic apparatus 8000, the ultrasonic beams 813 can be correctly focused without receiving adverse influences caused by such a strongly reflecting article 814.

INTERNAL ARRANGEMENT OF LOW-FREQUENCY COMPONENT ELIMINATING SECTION

Figure 44:
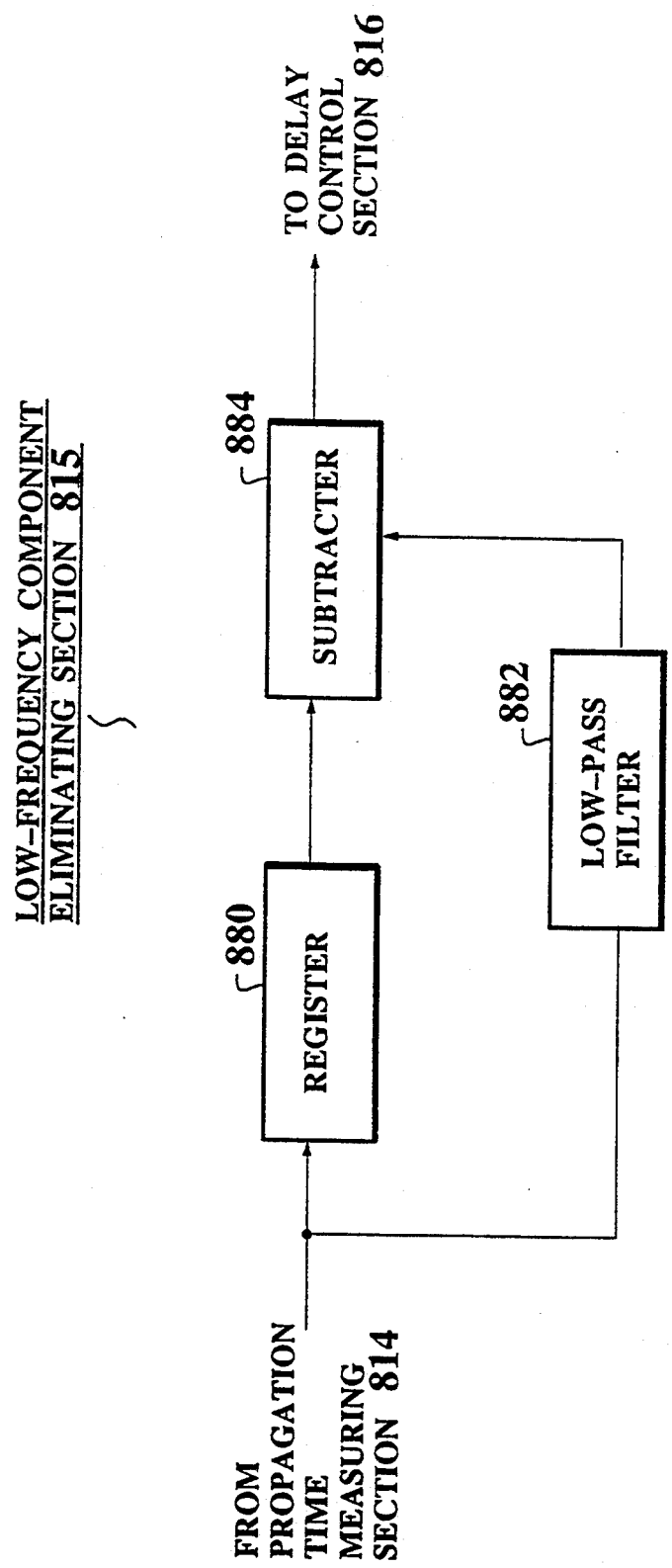

The low-frequency component eliminating section 815 functioning as the main feature of the eighth ultrasonic diagnostic apparatus 8000, may be constructed by various circuit arrangements, for example, by employing a known F.I.R. filter (not shown in detail). FIG. 44 represents another circuit arrangement of realizing the low-frequency component eliminating section 815. As apparent from FIG. 44, a register 880 is to store the above-described distribution curve data from the propagation time measuring section 814. Simultaneously, this curve data is supplied to a low-pass filter 882 to pass only a low-frequency component. A subtracter 884 subtracts this low-frequency component from the distribution curve data derived from the register 880, so that the delay-time correction signal from which the low-frequency component has been eliminated is obtained from the subtracter 884.

SIXTH BASIC IDEA

As is known in the art, generally speaking, a shape of ultrasonic transmission beam is varied due to various factors existing in an ultrasonic diagnostic system and also a biological body, e.g., an aperture of a transducer array, a focal distance, a frequency, a depth measured from the transducer aperture, and ultrasonic attenuation characteristics within a biological body.

Figure 45:
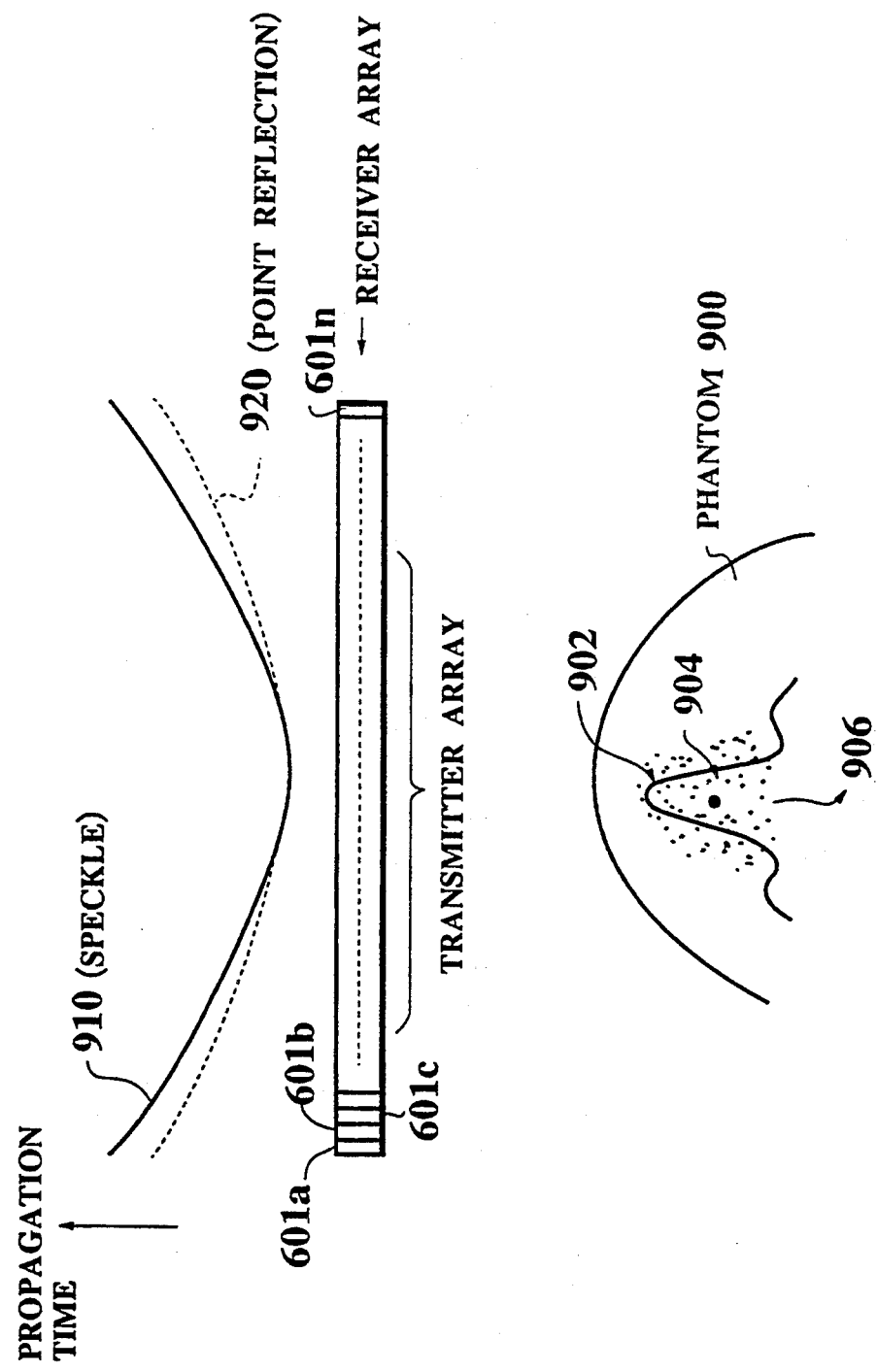

Referring now to FIG. 45, a sixth basic idea of the present invention will now be described more in detail.

In FIG. 45, reference numerals 601a to 601n (symbols "a" to "n" indicate integers) represent transducer elements arranged In an array form. All of these transducer elements 601a to 601n constitute a receiver array, whereas a center portion of these transducer elements constitute a transmitter array.

An ultrasonic pulse beam 902 is transmitted from the transmitter array to be focused onto a certain region within a phantom 900. The phantom 900 is made of very fine powder such as graphite which is uniformly mixed with agar. When the ultrasonic transmission beams 902 are reflected as reflection echoes from a speckle (i.e., graphite particles) 906 and also a point-shaped reflecting article 904, there is a difference in the propagation times of the reflection echoes. That is, as represented in FIG. 45, a solid line 910 indicates a propagation-time distribution curve in case that the reflection echoes are obtained from the speckle 906, whereas a dot line 920 denotes a propagation-time distribution curve in case that the reflection echoes are obtained from the point-shaped reflecting article 904. The difference between these propagation-time distribution times may causes deformation (not sharp shape) of the transmission beam 902.

Under such circumstances, even if fluctuation in the propagation times of the ultrasonic transmission pulses within such a phantom 900 having a uniform propagation medium is measured for correcting delay times of the transmission/reception signals, no precise delay time correction can be achieved because the shapes of the transmission pulses are deformed.

Accordingly, the sixth basic idea of the present invention is to solve such a problem. That is, according to sixth basic idea, since the shapes of the transmission beams 902 are varied by various conditions (array aperture, frequency, attenuation) of an ultrasonic diagnostic system and a biological body under medical examination, errors in the propagation times (namely, differences between propagation times of echoes reflected from the speckle 906 of the phantom 900 those from the point-shaped reflecting article 904 thereof) are previously obtained as calibration data. Subsequently, another propagation time data is acquired when a speckle of a biological body (not shown in detail) is actually scanned by the ultrasonic transmission pulses, and then the resultant propagation time data is subtracted by above-described calibration data. As a consequence, it is possible to measure a propagation time that is substantially correct precision with one when the measurement is performed with employment of the point-shaped reflecting article.

ARRANGEMENT OF NINTH ULTRASONIC DIAGNOSTIC APPARATUS

Figure 46:
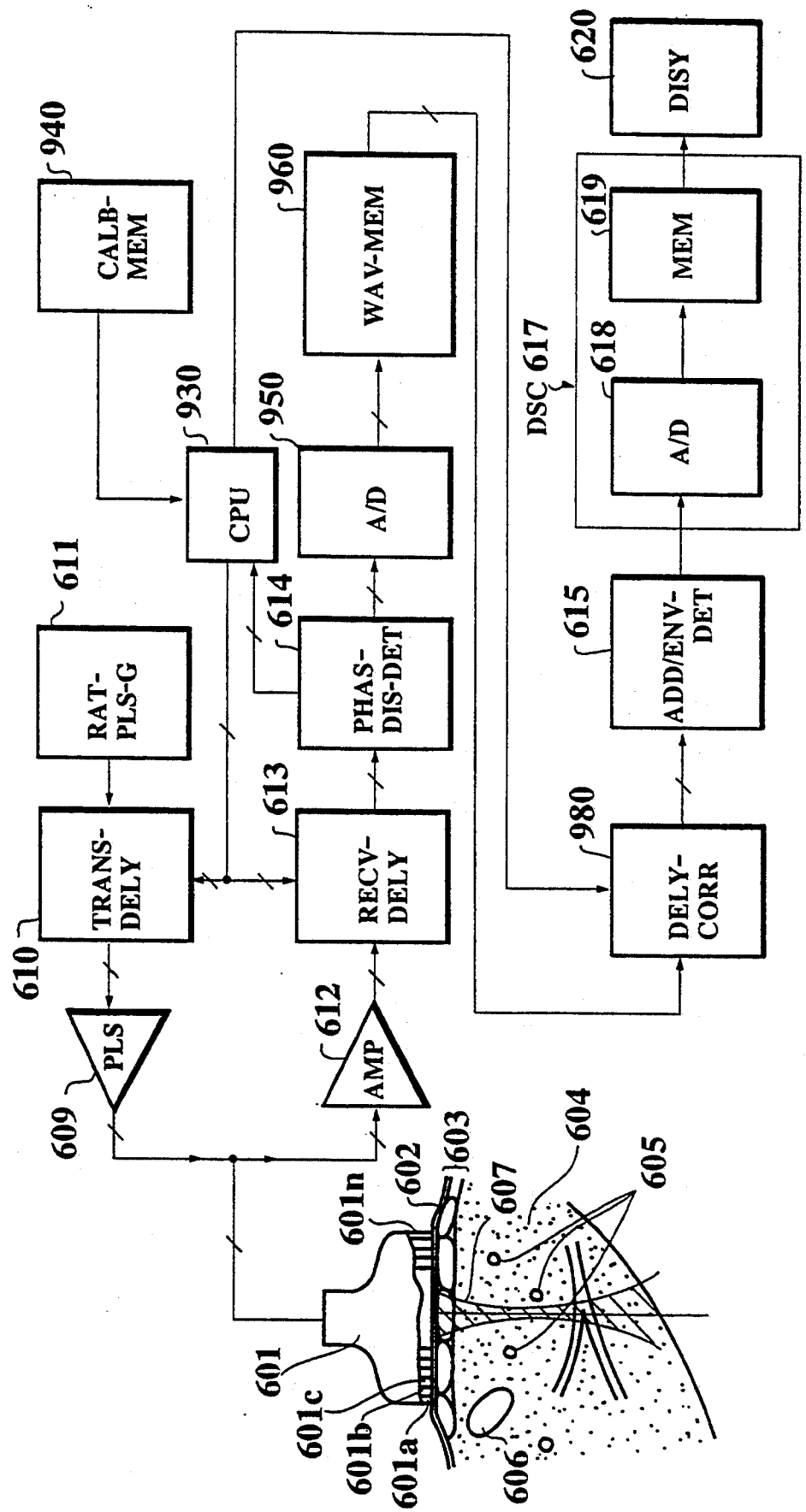

FIG. 46 represents an overall arrangement of an ultrasonic diagnostic apparatus 9000 according to a ninth preferred embodiment of the present invention, which is accomplished by the above-described sixth basic idea.

As apparent from FIGS. 46 and 35, since the most circuit arrangements of the ninth ultrasonic diagnostic apparatus 9000 is the same as those of the sixth ultrasonic diagnostic apparatus 6000, only a different circuit arrangement thereof will now be described.

First, the phantom 900 having such characteristics equivalent to ultrasonic attenuation characteristics of a biological body under medical examination is actually employed to experimentally obtain errors in propagation times for the respective reception transducer elements "601a" to "601n" (namely, propagation time differences between two measurement conditions, i.e., reflections from the point-shaped article 904 and the speckle 906). The resultant propagation-time error data are stored in the calibration data memory 940 as the calibration data.

Subsequently, instead of this phantom 900, a biological body under medical examination (not shown in detail) is ultrasonically scanned by the ninth ultrasonic diagnostic apparatus 9000 thereby to obtain propagation time data. Then, the propagation time data of the biological body are stored in the waveform memory 960 after being A/D-converted into digital propagation time data.

In the delay time correcting circuit 980, the propagation time data of the biological body are subtracted by the calibration data so that the above-described various errors can be finally eliminated from the propagation time data of the biological body, resulting in improving spacial resolution of ultrasonic images and also measurement precision of propagation time distortion.

What is claimed is:

1. An ultrasonic diagnostic apparatus comprising:
    ultrasonic transducer means having a plurality of ultrasonic transducer elements for transmitting ultrasonic pulses to an object under medical examination in response to energizing signals, and for receiving echoes therefrom to produce echo signals;
    quadrature phase detecting means for quadrature-phase-detecting the echo signals derived from the transducer means with reference to a reference signal to obtain as phase data a quadrature signal component and an in-phase signal component;
    phase-difference calculating means for processing said quadrature signal component and said in-phase signal component to obtain a phase difference between said quadrature signal component and said in phase signal component with reference to said reference signal;
    delay-time correcting value calculating means for processing said phase difference to obtain a delay time correcting value; and
    delay time controlling means for controlling said ultrasonic transducer means in such a manner that at least one delay time initially given to both of said energizing signals and said echo signals is corrected based on said delay-time correction value.

2. An ultrasonic diagnostic apparatus as claimed in claim 1, wherein said delay-time correcting value calculating means includes a means for further performing an interpolation process based on the actually received echo signals while only a preselected number of transducer elements are energized by the energizing signals, whereby the echo signals with respect to all transducer elements are obtained.

3. An ultrasonic diagnostic apparatus as claimed in claim 2, further comprising:
    a multiplexer unit for sequentially transferring the phase data obtained from the quadrature phase detecting means to the delay-time correcting value calculating means.

4. An ultrasonic diagnostic apparatus as claimed in claim 1, further comprising:
    phase correcting means interposed between the quadrature phase detecting means and the delay-time correcting value calculating means, for correcting phases of the phase data derived from the quadrature phase detecting means in such a manner that discontinuity points contained in phase distribution data of the phase data are coupled with each other so as to obtain continuous phase distribution data.

5. An ultrasonic diagnostic apparatus as claimed in claim 1, further comprising:
   initial delay-time applying means for initially applying predetermined initial delay-time to said echo signals before performing the quadrature phase detecting by said quadrature phase detecting means, whereby said phase difference is directly used as said delay-time correction value.

6. An ultrasonic diagnostic apparatus, comprising:
   ultrasonic transducer means having a plurality of ultrasonic transducer elements for transmitting ultrasonic pulses to an object under medical examination in response to energizing signals, and for receiving echoes therefrom to produce echo signals;
   quadrature phase detecting means for quadrature-phase-detecting the echo signals derived from the transducer means to obtain as phase data a quadrature signal component and an in-phase signal component;
   delay-time correcting value calculating means for processing both of said quadrature signal component and said in-phase signal component to obtain at least one delay time correcting value;
   delay time controlling means for controlling said ultrasonic transducer means in such a manner that at least one delay time initially given to both of said energizing signals and said echo signals is corrected based on said at least one delay time correcting value;
   phase correcting means interposed between the quadrature phase detecting means and the delay-time correcting value calculating means and including;
   a discontinuity correcting unit for first calculating a phase difference between the echo signals derived from adjacent transducer elements so as to search discontinuity points contained in the phase data and for secondly correcting the searched discontinuity points by adding to the phase data and bias values corresponding to the calculated phase differences; and
   a temporal direction averaging unit for averaging the phase data having the corrected discontinuities, whereby a focal point without phase shifts is formed by applying to the energizing pulses, a delay-time correcting value produced by the averaged phase data.

7. An ultrasonic diagnostic apparatus comprising:
   ultrasonic transducer means having a plurality of transducer elements for transmitting ultrasonic pulses to a specific region within an object under medical examination in response to energizing signals, and for receiving echoes from the specific region to produce echo signals;
   first delay-time correcting value calculating means for calculating first delay-time correcting values with respect to first transmitting/receiving delay times for the respective transducer elements by calculating propagation time differences among the echo signals from focal points of the ultrasonic pulses within the specific region;
   second delay-time correcting value calculating means for calculating second delay-time correcting values with respect to second transmitting/receiving delay times for tile transducer elements used to receive the echo signals from a region other than the specific region by interpolating the first delay-time correcting values; and,
   delay controlling means for controlling predetermined transmitting/receiving delay times with respect to said specific region based on said first delay-time correcting values and also with respect to said region other than said specific region based on said second delay-time correcting values.

8. An ultrasonic diagnostic apparatus as claimed in claim 7, wherein said first delay-time correcting value calculating means includes at least:
   a plurality of correlation calculating units for temporally limiting the echo signals received from the adjacent transducer elements so as to correlate two sets of temporally limited echo signals;
   a plurality of peak detecting units for detecting peak values of the correlated echo signals in order to obtain a phase difference between the adjacent echo signals; and,
   an accumulator unit for accumulating the phase differences obtained from the peak detecting units thereby to obtain said first delay-time correcting values.

9. An ultrasonic diagnostic apparatus as claimed in claim 7, wherein said second delay-time correcting value calculating means includes interpolating means for inner-interpolating said first delay-time correcting values to obtain said second delay-time correcting values.

10. An ultrasonic diagnostic apparatus as claimed in claim 9, wherein said inner-interpolation is a linear interpolation.

11. An ultrasonic diagnostic apparatus as claimed in claim 7, wherein said second delay-time correcting value calculating means includes interpolating means for outer-interpolating said first delay-time correcting values to obtain said second delay-time correcting values.

12. An ultrasonic diagnostic apparatus as claimed in claim 11, wherein said outer-interpolation is a linear interpolation.

13. An ultrasonic diagnostic apparatus comprising:
   ultrasonic transducer means having a plurality of ultrasonic transducer elements, for transmitting ultrasonic pulses to an object under medical examination in response to energizing signals, and for receiving echoes therefrom to produce echo signals;
   judging means for judging whether or not the received echo signals are valid data used to correct delay times for the energizing signals and echo signals;
   phase-distortion detecting means for detecting phase distortion contained in the echo signals acquired when said judging means judges that the received echo signals are valid data;
   delay-time correcting value calculating means for calculating at least one of transmission/reception delay-time correcting values based on a result of the phase-distortion detecting means; and,
   delay controlling means for controlling at least one of transmission/reception delay time data previously given to the energizing signals and echo signals based on said one of calculated transmission/reception delay-time correcting values.

14. An ultrasonic diagnostic apparatus as claimed in claim 13, wherein said Judging means is a histogram forming circuit for forming a histogram of strengths of the echo signals received by said ultrasonic transducer means and for analyzing a pattern reflected in said histogram so as to judge whether or not the received echo signals are said valid data.

15. An ultrasonic diagnostic apparatus as claimed in claim 14, wherein said histogram forming circuit is comprised of a random access memory having an address table, an increment unit and a storage unit.

16. An ultrasonic diagnostic apparatus as claimed in claim 13, wherein said judging means includes comparing means for comparing an average value of the echo signals with a predetermined threshold level in order to Judge whether or not the received echo signals are said valid data.

17. An ultrasonic diagnostic apparatus as claimed in claim 16, wherein said Judging means is comprised of a shift register 625, first and second accumulators and a subtracter.

18. An ultrasonic diagnostic apparatus comprising:
ultrasonic transducer means having a plurality of ultrasonic transducer elements, for transmitting ultrasonic pulses to an object under medical examination in response to energizing signals, and for receiving echoes therefrom to produce echo signals;
propagation-time-difference detecting means for detecting propagation time differences among the echo signals derived from the transducer elements as propagation time distribution data;
delay-time value calculating means for calculating first delay-time correcting values with respect to previously set transmission/reception delay time data based on the detected propagation time difference data;
eliminating means for eliminating an unwanted signal component representative of unwanted reflecting articles within the biological body from the propagation time difference data thereby to obtain second delay-time correcting values; and,
delay controlling means for controlling delay time data previously given to the energizing signals and echo signals by correcting said first delay-time correcting values based on said second delay-time correcting values.

19. An ultrasonic diagnostic apparatus as claimed in claim 18, wherein said eliminating means is a low-frequency component eliminating unit comprised of a register, a subtracter and a low-pass filter so as to eliminate a low-frequency component as said unwanted signal component from said propagation time difference data.

20. An ultrasonic diagnostic apparatus comprising:
ultrasonic transducer means having a plurality of ultrasonic transducer elements for transmitting ultrasonic pulses to an object under medical examination in response to energizing signals, and for receiving echoes therefrom to produce echo signals;
propagation-time-difference detecting means for detecting first propagation time differences among the echo signals derived via the transducer elements from the biological body;
delay-time correcting value calculating means for calculating transmission/reception delay-time correcting values based on the detected propagation-time differences;
means for obtaining delay-time calibration values from second propagation time differences among the echo signals derived via the transducer elements from a phantom having characteristics substantially equivalent to ultrasonic attenuation characteristics of said biological body previously measured by said ultrasonic transducer means; and
delay controlling means for controlling said ultrasonic transducer means in such a manner that delay times initially given to both of said energizing signals and said echo signals are corrected based upon both of said transmission/reception delay-time correcting values and said delay time calibration values.

21. An ultrasonic diagnostic apparatus as claimed in claim 20, further comprising:
a waveform memory for storing said first propagation time differences which have been detected by actually scanning said biological body with employment of the transducer means.

22. An ultrasonic diagnostic apparatus comprising:
ultrasonic transducer elements for transmitting ultrasonic pulses to an object under medical examination in response to energizing signals, and for receiving echoes therefrom to produce echo signals;
quadrature phase detecting means for quadrature-phase-detecting two echo signals derived from two successively positioned transducer elements based upon one of said two echo signals as a reference signal to obtain as phase data a quadrature signal component and an in-phase signal component, said quadrature signal detection being carried out for other two echo signals produced from the remaining two adjacent transducer elements of the ultrasonic transducer means;
phase-difference detecting means for calculating a ratio of said in-phase signal component to said quadrature signal component, thereby obtaining a phase difference between said first and second echo signals; and
delay time controlling means for controlling said ultrasonic transducer means in such a manner that at least one delay time initially given to both of said energizing signals is corrected based on said phase difference.

* * * * *

UNITED STATES PATENT AND TRADEMARK OFFICE
CERTIFICATE OF CORRECTION

PATENT NO. : 5,348,013
DATED : September 20, 1994
INVENTOR(S) : Ryoichi KANDA et al.

It is certified that error appears in the above-indentified patent and that said Letters Patent is hereby corrected as shown below:

Claim 5, Column 31, Line 6, change "detecting" to --detection--.

Claim 6, Column 31, Line 33, change "including;" to --including:--.

Claim 7, Column 31, Line 65, change "tile" to --the--.

Claim 14, Column 32, Line 65, change "Judging" to --judging--

Claim 16, Column 33, Line 11, change "Judge" to --judge--.

Claim 17, Column 33, Line 14, change "Judging" to --judging--.

UNITED STATES PATENT AND TRADEMARK OFFICE
CERTIFICATE OF CORRECTION

PATENT NO. : 5,348,013
DATED : September 20, 1994
INVENTOR(S) : Ryoichi KANDA et al.

It is certified that error appears in the above-indentified patent and that said Letters Patent is hereby corrected as shown below:

Claim 22, Column 34, Line 32, before "ultrasonic transducer", insert -- ultrasonic transducer means having a plurality of--.

Abstract, line 15, change "anti" to --and--.

Signed and Sealed this

Thirteenth Day of June, 1995

Attest:

BRUCE LEHMAN

Attesting Officer

Commissioner of Patents and Trademarks